United States Patent
Khairkhahan et al.

(10) Patent No.: US 7,044,134 B2
(45) Date of Patent: May 16, 2006

(54) METHOD OF IMPLANTING A DEVICE IN THE LEFT ATRIAL APPENDAGE

(75) Inventors: Alexander K. Khairkhahan, Palo Alto, CA (US); Andrew G. C. Frazier, Mountain View, CA (US); Alan R. Klenk, San Jose, CA (US); Marc S. Kreidler, Sunnyvale, CA (US); Stewart M. Kume, Belmont, CA (US); Darrell H. Ogi, Sunnyvale, CA (US); Chad C. Roue, Fremont, CA (US); Erik J. van der Burg, Sunnyvale, CA (US)

(73) Assignee: ev3 Sunnyvale, Inc, Plymouth, MN (US)

( * ) Notice: Subject to any disclaimer, the term of this patent is extended or adjusted under 35 U.S.C. 154(b) by 313 days.

(21) Appl. No.: 10/033,371

(22) Filed: Oct. 19, 2001

(65) Prior Publication Data

US 2002/0111647 A1 Aug. 15, 2002

Related U.S. Application Data

(60) Division of application No. 10/033,371, filed on Oct. 19, 2001, which is a continuation-in-part of application No. 09/435,562, filed on Nov. 8, 1999.

(51) Int. Cl.
*A61B 17/00* (2006.01)

(52) U.S. Cl. ............... 128/887; 606/198; 606/200; 606/213; 604/107

(58) Field of Classification Search ............... 128/887, 128/898; 606/190–200, 213, 1, 108, 159, 606/167, 151; 604/96.01–109, 508–510

See application file for complete search history.

(56) References Cited

U.S. PATENT DOCUMENTS

| 3,402,710 A | 9/1968 | Paleschuck |
| 3,540,431 A | 11/1970 | Uddin |
| 3,638,652 A | 2/1972 | Kelly |

(Continued)

FOREIGN PATENT DOCUMENTS

| WO | WO 95/04132 | 2/1995 | |
| WO | WO 96/40356 | 12/1996 | |
| WO | WO 98/27868 | 7/1998 | |
| WO | WO 99/23976 | 5/1999 | |
| WO | WO 99/44510 | 9/1999 | |
| WO | WO 00/16705 | 3/2000 | |
| WO | WO 00/27292 | 5/2000 | |
| WO | WO 00/67669 | 11/2000 | |
| WO | WO 01/15629 A1 | 3/2001 | |
| WO | WO 01/30266 A1 * | 5/2001 | ............ 604/508 |
| WO | WO 01/30267 A1 | 5/2001 | |
| WO | WO 01/30268 A1 | 5/2001 | |
| WO | WO 02/15793 A2 | 2/2002 | |
| WO | WO 02/24106 A2 | 3/2002 | |

OTHER PUBLICATIONS

International Search Report for PCT/US99/26325 dated Feb. 15, 2000.
Written Opinion for PCT/US02/33808 dated Nov. 17, 2003.

(Continued)

*Primary Examiner*—Glenn K. Dawson
(74) *Attorney, Agent, or Firm*—Knobbe Martens Olson & Bear LLP

(57) ABSTRACT

An adjustable occlusion device and a method of implanting the device in a body lumen such as the left atrial appendage. The occlusion device is removably carried by a deployment catheter. The device may be enlarged or reduced to facilitate optimal placement or removal. Methods are also disclosed.

39 Claims, 13 Drawing Sheets

U.S. PATENT DOCUMENTS

| | | | |
|---|---|---|---|
| 3,844,302 A | 10/1974 | Klein | |
| 3,874,388 A | 4/1975 | King et al. | |
| 4,007,743 A | 2/1977 | Blake | |
| 4,309,776 A | 1/1982 | Berguer | |
| 4,341,218 A | 7/1982 | Ü | |
| 4,603,693 A | 8/1986 | Contra et al. | |
| 4,665,906 A | 5/1987 | Jervis | |
| 4,681,588 A | 7/1987 | Ketharanathan | |
| 4,710,192 A | 12/1987 | Liotta et al. | |
| 4,917,089 A | 4/1990 | Sideris | |
| 4,921,484 A | 5/1990 | Hillstead | |
| 5,041,090 A | 8/1991 | Scheglov et al. | |
| 5,042,707 A | 8/1991 | Taheri | |
| 5,064,435 A | 11/1991 | Porter | |
| 5,071,407 A | 12/1991 | Termin et al. | |
| 5,078,736 A | 1/1992 | Behl | |
| 5,108,418 A | 4/1992 | Lefebvre | |
| 5,108,420 A | 4/1992 | Marks | |
| 5,108,474 A | 4/1992 | Riedy et al. | |
| 5,122,136 A | 6/1992 | Guglielmi et al. | |
| 5,171,259 A | 12/1992 | Inoue | |
| 5,176,692 A | 1/1993 | Wilk et al. | |
| 5,192,301 A | 3/1993 | Kamiya et al. | |
| 5,234,458 A | 8/1993 | Metais | |
| 5,258,000 A | 11/1993 | Gianturco | |
| 5,258,042 A | 11/1993 | Mehta | |
| 5,284,488 A | 2/1994 | Sideris | |
| 5,304,184 A | 4/1994 | Hathaway et al. | |
| 5,306,234 A | 4/1994 | Johnson | |
| 5,334,217 A | 8/1994 | Das | |
| 5,350,399 A | 9/1994 | Erlebacher et al. | |
| 5,375,612 A | 12/1994 | Cottenceau et al. | |
| 5,417,699 A | 5/1995 | Klein et al. | |
| 5,425,744 A | 6/1995 | Fagan et al. | |
| 5,433,727 A | 7/1995 | Sideris | |
| 5,443,454 A | 8/1995 | Tanabe et al. | |
| 5,443,478 A | 8/1995 | Purdy | |
| 5,451,235 A | 9/1995 | Lock et al. | |
| 5,464,408 A | 11/1995 | Duc | |
| 5,490,856 A | 2/1996 | Person et al. | |
| 5,522,790 A | 6/1996 | Moll et al. | |
| 5,522,836 A | 6/1996 | Palermo | |
| 5,527,322 A | 6/1996 | Klein et al. | |
| 5,527,338 A | 6/1996 | Purdy | |
| 5,614,204 A | 3/1997 | Cochrum | |
| 5,634,936 A | 6/1997 | Linden et al. | |
| 5,643,292 A | 7/1997 | Hart | |
| 5,669,933 A | 9/1997 | Simon et al. | |
| 5,693,067 A | 12/1997 | Purdy | |
| 5,702,421 A | 12/1997 | Schneidt | |
| 5,709,224 A | 1/1998 | Behl et al. | |
| 5,709,707 A | 1/1998 | Lock et al. | |
| 5,725,552 A | 3/1998 | Kotula et al. | |
| 5,725,568 A | 3/1998 | Hastings | |
| 5,733,294 A | 3/1998 | Forber et al. | |
| 5,735,290 A | 4/1998 | Sterman et al. | |
| 5,749,894 A | 5/1998 | Engelson | |
| 5,766,219 A | 6/1998 | Horton | |
| 5,776,097 A | 7/1998 | Massoud | |
| 5,782,860 A | 7/1998 | Epstein et al. | |
| 5,830,228 A | 11/1998 | Knapp et al. | |
| 5,836,968 A | 11/1998 | Simon et al. | |
| 5,843,118 A | 12/1998 | Sepetka et al. | |
| 5,849,005 A | 12/1998 | Garrison et al. | |
| 5,853,422 A | 12/1998 | Huebsch et al. | |
| 5,865,791 A | 2/1999 | Whayne et al. | |
| 5,879,366 A | 3/1999 | Shaw et al. | |
| 5,891,558 A | 4/1999 | Bell et al. | |
| 5,904,680 A * | 5/1999 | Kordis et al. | 606/41 |
| 5,906,207 A | 5/1999 | Shen | |
| 5,935,148 A | 8/1999 | Villar et al. | |
| 6,004,348 A | 12/1999 | Banas et al. | |
| 6,007,557 A | 12/1999 | Ambrisco et al. | |
| 6,076,012 A * | 6/2000 | Swanson et al. | 604/21 |
| 6,079,414 A | 6/2000 | Roth | |
| 6,080,182 A | 6/2000 | Shaw et al. | |
| 6,096,053 A | 8/2000 | Bates | |
| 6,124,523 A | 9/2000 | Banas et al. | |
| 6,132,438 A | 10/2000 | Fleischman et al. | |
| 6,139,573 A | 10/2000 | Sogard et al. | |
| 6,152,144 A | 11/2000 | Lesh et al. | |
| 6,171,329 B1 | 1/2001 | Shaw et al. | |
| 6,214,029 B1 | 4/2001 | Thill et al. | |
| 6,231,589 B1 | 5/2001 | Wessman et al. | |
| 6,290,674 B1 | 9/2001 | Roue et al. | |
| 6,368,338 B1 | 4/2002 | Kónya et al. | |
| 6,371,971 B1 | 4/2002 | Tsugita et al. | |
| 6,391,044 B1 | 5/2002 | Yadav et al. | |
| 6,402,746 B1 * | 6/2002 | Whayne et al. | 606/41 |
| 6,440,152 B1 | 8/2002 | Gainor et al. | |
| 6,443,972 B1 | 9/2002 | Bosma et al. | |
| 6,468,291 B1 | 10/2002 | Bates et al. | |
| 6,468,301 B1 | 10/2002 | Amplatz et al. | |
| 6,511,496 B1 | 1/2003 | Huter et al. | |
| 6,551,303 B1 * | 4/2003 | Van Tassel et al. | 604/508 |
| 6,551,344 B1 | 4/2003 | Thill | |
| 6,558,405 B1 | 5/2003 | McInnes | |
| 6,562,058 B1 | 5/2003 | Seguin et al. | |
| 6,599,308 B1 | 7/2003 | Amplatz | |
| 6,652,555 B1 | 11/2003 | VanTassel et al. | |
| 6,652,556 B1 | 11/2003 | VanTassel et al. | |
| 6,689,150 B1 * | 2/2004 | VanTassel et al. | 606/200 |
| 2001/0034537 A1 | 10/2001 | Shaw et al. | |
| 2001/0037141 A1 | 11/2001 | Yee et al. | |
| 2002/0022860 A1 | 2/2002 | Borillo et al. | |
| 2002/0035374 A1 | 3/2002 | Borillo et al. | |
| 2002/0062133 A1 | 5/2002 | Gilson et al. | |
| 2002/0099439 A1 | 7/2002 | Schwartz et al. | |
| 2002/0138094 A1 | 9/2002 | Borillo et al. | |
| 2002/0138097 A1 | 9/2002 | Ostrovsky et al. | |
| 2003/0023262 A1 * | 1/2003 | Welch | 606/194 |
| 2003/0023266 A1 | 1/2003 | Borillo et al. | |
| 2003/0057156 A1 | 3/2003 | Peterson et al. | |
| 2003/0120337 A1 | 6/2003 | Van Tassel et al. | |
| 2003/0181942 A1 | 9/2003 | Sutton et al. | |
| 2003/0191526 A1 | 10/2003 | Van Tassel et al. | |

OTHER PUBLICATIONS

Copending U.S. Appl. No. 10/364,910, filed Feb. 11, 2003, in the name of Erik J. Van Der Burg et al.; a Preliminary Amendment, filed Jul. 24, 2003.

Copending U.S. Appl. No. 10/426,130, filed Apr. 28, 2003, in the name of Andrew G. C. Frazier, et al.

Copending U.S. Appl. No. 10/441,492, filed May 19, 2003, in the name of Alexander K. Khairkhahan, et al.; an Office Action mailed Dec. 22, 2003.

Copending U.S. Appl. No. 10/441,468, filed May 19, 2003, in the name of Alexander K. Khairkhahan, et al.; a Preliminary Amendment filed Oct. 24, 2003.

Copending U.S. Appl. No. 10/674,553, filed Sep. 30, 2003, in the name of Erik J. van der Burg, et al.; a Preliminary Amendment mailed Feb. 6, 2004.

International Search Report from co-pending PCT/US02/33808, dated May 20, 2003.

* cited by examiner

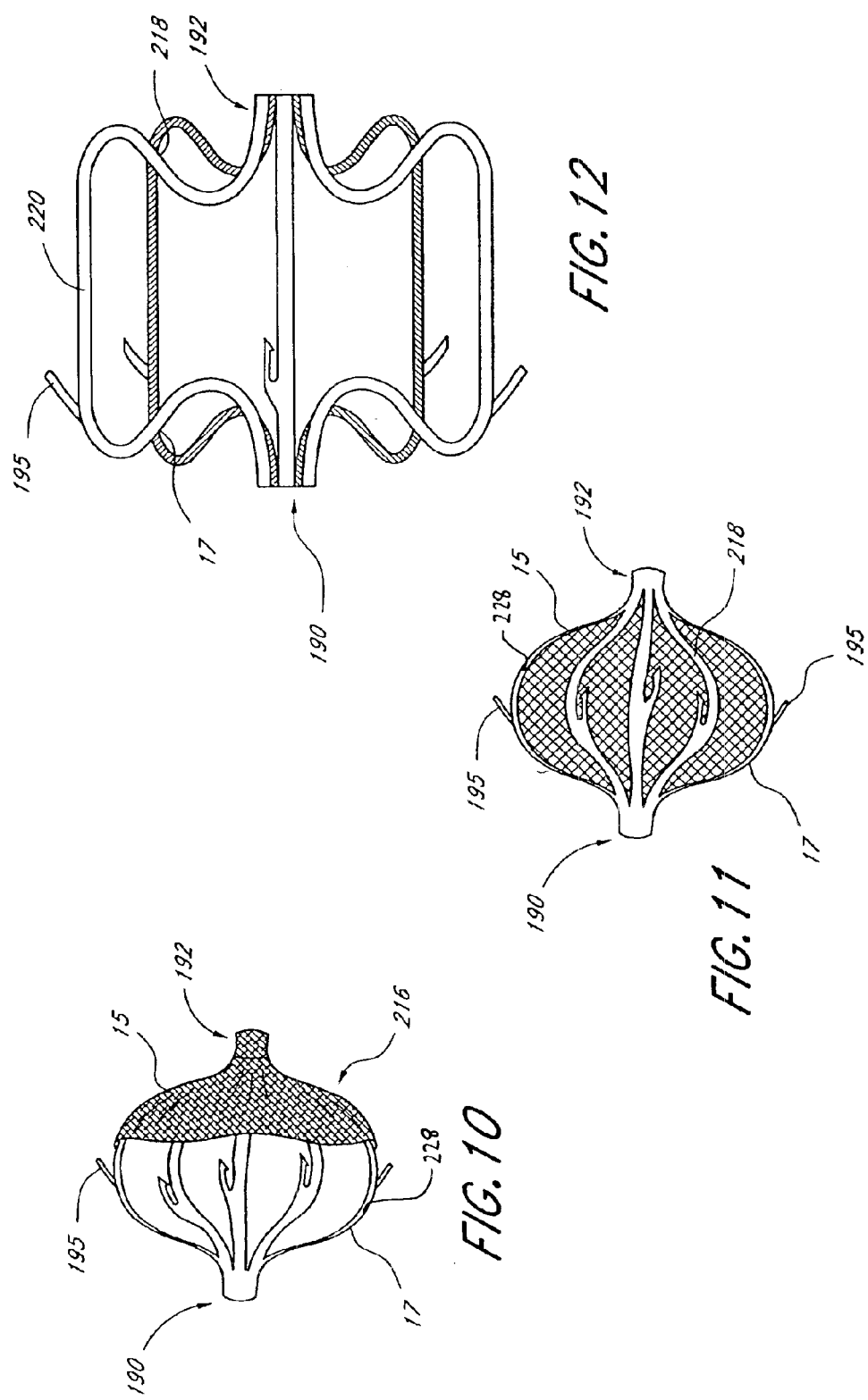

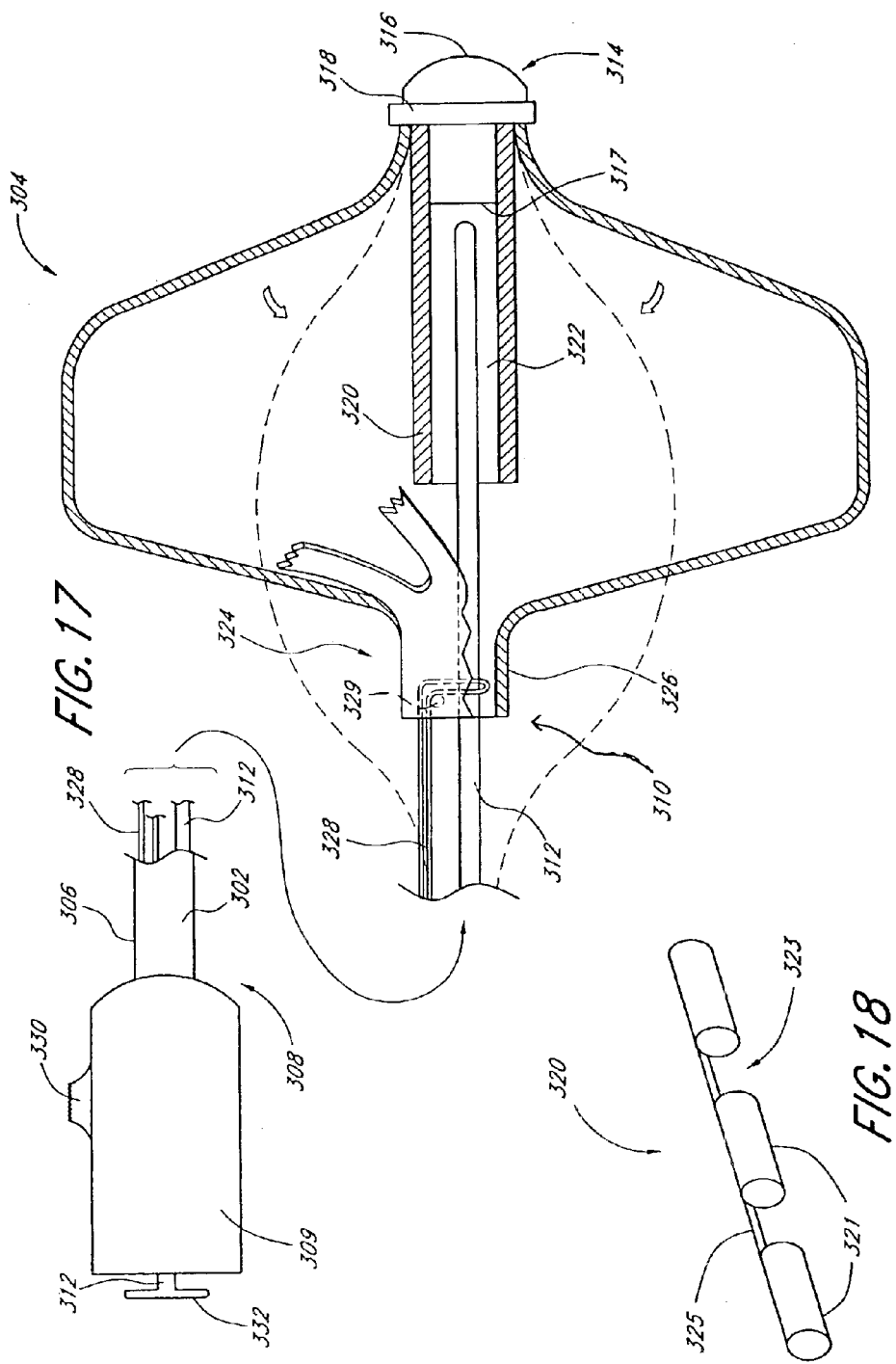

METHOD OF IMPLANTING A DEVICE IN THE LEFT ATRIAL APPENDAGE

This is a divisional of U.S. patent application Ser. No. 10/033,371, filed Oct. 19, 2001, which is a continuation-in-part of U.S. patent application Ser. No. 09/435,562, filed Nov. 8, 1999, the disclosures of which are incorporated in their entirety herein by reference.

BACKGROUND OF THE INVENTION

Embolic stroke is the nation's third leading killer for adults, and is a major cause of disability. There are over 700,000 strokes per year in the United States alone. Of these, roughly 100,000 are hemoragic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996.61(2):755–9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996.61(2):515.

Despite the various efforts in the prior art, there remains a need for a minimally invasive method and associated devices for reducing the risk of thrombus formation in the left atrial appendage.

SUMMARY OF THE INVENTION

There is provided in accordance with one aspect of the present invention an adjustable occlusion device deployment system, for implanting an occlusion device within a tubular structure in the body. The system comprises an occlusion device, movable between a reduced cross section and an enlarged cross section. A deployment catheter is provided, releasably attached to the occlusion device. A releasable lock for retaining the occlusion device is provided on the catheter, along with a core, for changing the cross section of the occlusion device.

The occlusion device comprises an expandable frame, which may have at least two and preferably at least about six spokes. In one embodiment, the occlusion device has sixteen spokes. Each spoke is moveable from an axial orientation when the occlusion device is in a reduced cross section, to an inclined orientation when the occlusion device is in an enlarged cross section. Preferably, at least one tissue attachment element is provided on the occlusion device.

In accordance with another aspect of the present invention, there is provided an occlusion device for occluding a tubular body structure. The device comprises a plurality of spokes, which are moveable between an axial orientation and an inclined orientation. A threaded aperture is carried by the device, and a stop surface is also carried by the device. A threaded core is rotatable within the aperture, to cause the core to contact the stop surface and axially elongate the device.

In accordance with a further aspect of the present invention, there is provided an implantable device. The device comprises a radially enlargeable frame having a proximal end and a distal end. A proximally facing stop surface is provided within the frame, and a threaded aperture is positioned in the frame, proximally of the stop surface. Distal axial advancement of a threaded core through the threaded aperture distally advances the stop surface, thereby axially elongating and radially reducing the implantable device. In one embodiment, the implantable device is an occlusion device. In an alternate embodiment, the implantable device is a filter.

In accordance with another aspect of the present invention, there is provided an occlusion device implantation system. The system comprises a deployment catheter, having an elongate flexible body with a proximal end and a distal end. An anti-rotation lock is provided on the body. A rotatable core extends axially through the body, and a radially expandable implant is releasably connected to the distal end of the body.

In accordance with a further aspect of the present invention, there is provided a method of implanting a device in the left atrial appendage. The method comprises the steps of providing a deployment catheter, having an elongate flexible body with a proximal end and a distal end, a control on the proximal end and a device removably carried by the distal end. At least a portion of the device is positioned within the left atrial appendage, and the control is manipulated to enlarge the device under positive force.

In one application of the invention, the manipulating step comprises rotating the control. In general, the device comprises an expandable frame having at least two and preferably at least about six spokes. Each spoke is movable from an axial orientation when the device is in a reduced cross section to an inclined orientation when the device is in an enlarged cross section.

In accordance with a further aspect of the present invention, there is provided a method of removing a device having tissue anchors thereon, from a site in the body. The method comprises the steps of positioning a retrieval catheter with respect to the device such that the anchors are within a flared distal end on the retrieval catheter. The diameter of the flared distal end is reduced, with the anchors therein. The retrieval catheter is thereafter removed from the site. In one aspect of the method, the reducing step comprises positioning the flared distal end within an outer tubular sleeve.

In accordance with a further aspect of the present invention, there is provided a retrieval catheter for retrieving a device from an implantation site within the body. The retrieval catheter comprises an elongate flexible body, having a proximal end and a distal end. A grasping structure is provided on or carried within the flexible body, for grasping the device, and a flared tubular sleeve is provided for surrounding at least a portion of the device. An outer tubular sleeve, for surrounding the flared tubular sleeve is also provided. The flared tubular sleeve in one embodiment comprises a plurality of petals, which are movable between an axial orientation and an inclined orientation.

Further features and advantages of the present invention will become apparent to those of ordinary skill in the art in view of the detailed description of preferred embodiments which follows, when considered together with the attached drawings and claims.

BRIEF DESCRIPTION OF THE DRAWINGS

FIGS. 10 and 11 are side elevational schematic representations of partial and complete barrier layers on the occlusion device of FIG. 7.

FIG. 12 is a side elevational schematic view of an alternate occlusion device in accordance with the present invention.

FIG. 17 is a schematic view of a deployment system in accordance with the present invention.

FIG. 18 is a perspective view of a flexible guide tube for use in the configurations of FIG. 17 and/or FIG. 19.

DETAILED DESCRIPTION OF THE PREFERRED EMBODIMENT

Figure 1:
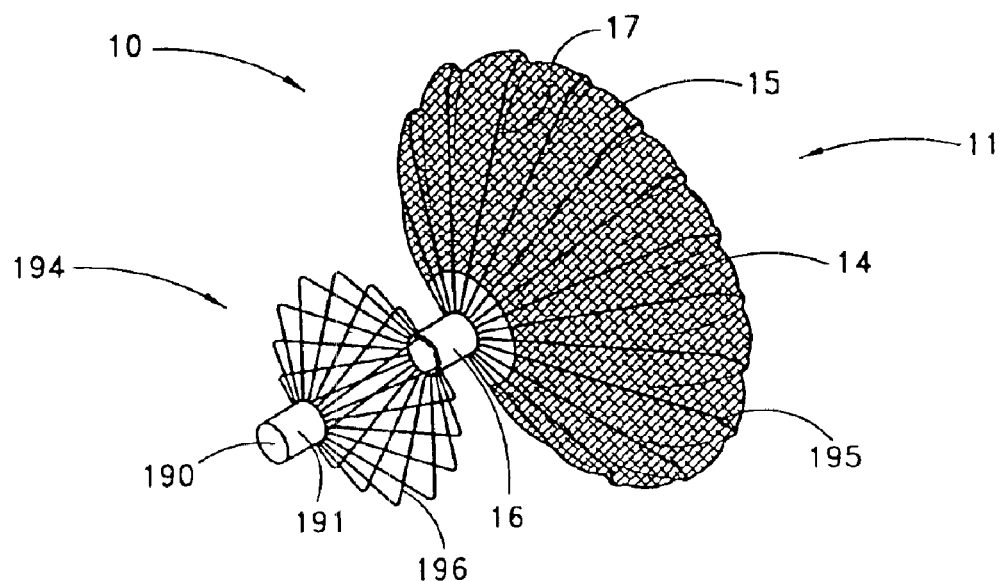
FIG. 1 is a perspective view of an occlusion device in accordance with the present invention.
Figure 2:
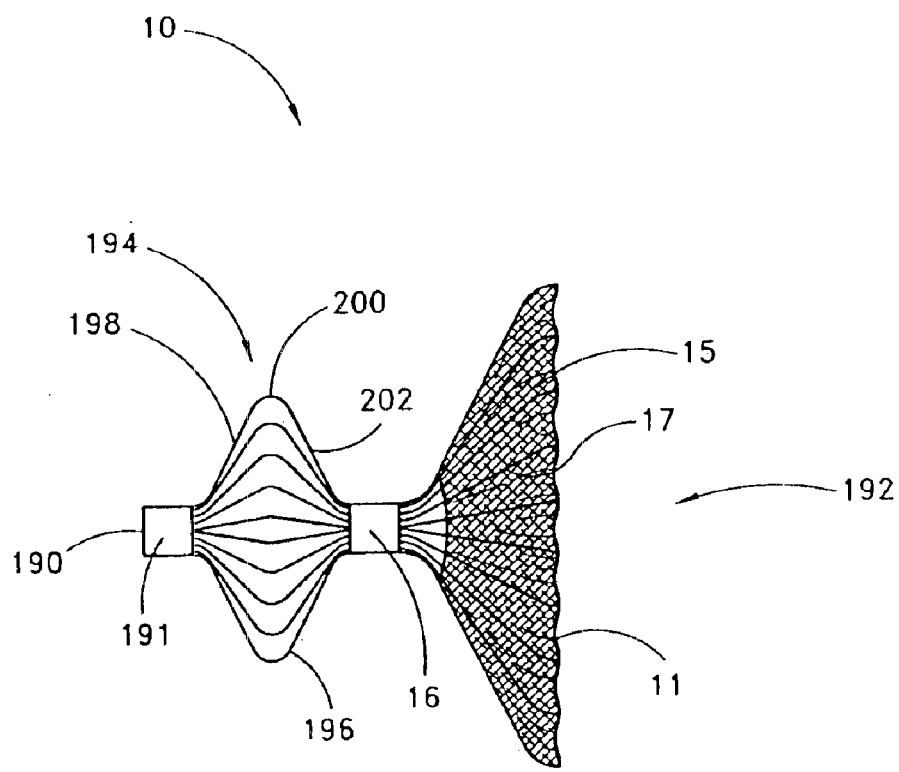
FIG. 2 is a side elevational view of the occlusion device shown in FIG. 1.

Referring to FIGS. 1 and 2, there is illustrated one embodiment of the occlusion device 10 in accordance with the present invention. Although the present invention will be described primarily in the context of an occlusion device, the present inventors also contemplate omitting the fabric cover or enlarging the pore size to produce implantable filters or other devices which are enlargeable at a remote implantation site.

The occlusion device 10 comprises an occluding member 11 comprising a frame 14 and a barrier 15. In the illustrated embodiment, the frame 14 comprises a plurality of radially outwardly extending spokes 17 each having a length within the range of from about 0.5 cm to about 2 cm from a hub 16. In one embodiment, the spokes have an axial length of about 1.5 cm. Depending upon the desired introduction crossing profile of the collapsed occlusion device 10, as well as structural strength requirements in the deployed device, anywhere within the range of from about 3 spokes to about 40 spokes may be utilized. In some embodiments, anywhere from about 12 to about 24 spokes are utilized, and, 18 spokes are utilized in one embodiment.

The spokes are advanceable from a generally axially extending orientation such as to fit within a tubular introduction catheter to a radially inclined orientation as illustrated in FIG. 1 and FIG. 2 following deployment from the catheter. In a self-expandable embodiment, the spokes are biased radially outwardly such that the occlusion member expands to its enlarged, implantation cross-section under its own bias following deployment from the catheter. Alternatively, the occlusion member may be enlarged using any of a variety of enlargement structures such as an inflatable balloon, or a catheter for axially shortening the occlusion member, as is discussed further below.

Preferably, the spokes comprise a metal such as stainless steel, Nitinol, Elgiloy, or others which can be determined through routine experimentation by those of skill in the art. Wires having a circular or rectangular cross-section may be utilized depending upon the manufacturing technique. In one embodiment, rectangular cross section spokes are cut such as by known laser cutting techniques from tube stock, a portion of which forms the hub 16.

The barrier 15 may comprise any of a variety of materials which facilitate cellular in-growth, such as ePTFE. The suitability of alternate materials for barrier 15 can be determined through routine experimentation by those of skill in the art. The barrier 15 may be provided on either one or both axially facing sides of the occlusion member. In one embodiment, the barrier 15 comprises two layers, with one layer on each side of the frame 14. The two layers may be bonded to each other around the spokes 17 in any of a variety of ways, such as by heat bonding with or without an intermediate bonding layer such as polyethylene or FEP, adhesives, sutures, and other techniques which will be apparent to those of skill in the art in view of the disclosure herein. The barrier 15 preferably has a thickness of no more than about 0.003" and a porosity within the range of from about 5 μm to about 60 μm.

The barrier 15 in one embodiment preferably is securely attached to the frame 14 and retains a sufficient porosity to facilitate cellular ingrowth and/or attachment. One method of manufacturing a suitable composite membrane barrier 15 is illustrated in FIGS. 13–16. As illustrated schematically in FIG. 13, a bonding layer 254 preferably comprises a mesh or other porous structure having an open surface area within the range of from about 10% to about 90%. Preferably, the open surface area of the mesh is within the range of from about 30% to about 60%. The opening or pore size of the bonding layer 254 is preferably within the range of from about 0.005 inches to about 0.050 inches, and, in one embodiment, is about 0.020 inches. The thickness of the bonding layer 254 can be varied widely, and is generally within the range of from about 0.0005 inches to about 0.005 inches. In a preferred embodiment, the bonding layer 254 has a thickness of about 0.001 to about 0.002 inches. One suitable polyethylene bonding mesh is available from Smith and Nephew, under the code SN9.

Figure 14:
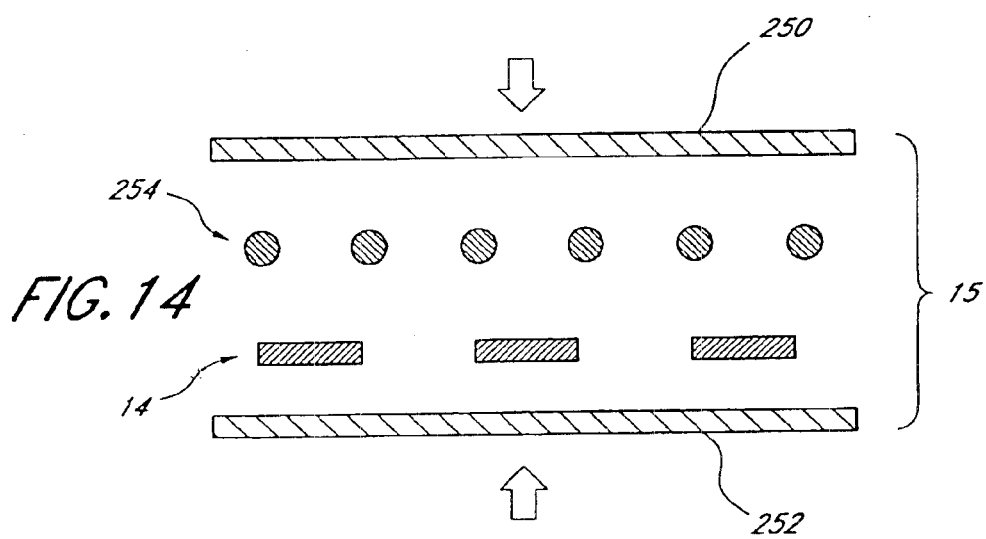
FIG. 14 is an exploded cross sectional view of the components of a composite barrier member in accordance with the present invention.

Referring to FIG. 14, the bonding layer 254 is preferably placed adjacent one or both sides of a spoke or other frame element 14. The bonding layer 254 and frame 14 layers are then positioned in-between a first membrane 250 and a second membrane 252 to provide a composite membrane stack. The first membrane 250 and second membrane 252 may comprise any of a variety of materials and thicknesses, depending upon the desired functional result. Generally, the membrane has a thickness within the range of from about 0.0005 inches to about 0.010 inches. In one embodiment, the membranes 250 and 252 each have a thickness on the order of from about 0.001 inches to about 0.002 inches, and comprise porous ePTFE, having a porosity within the range of from about 10 microns to about 100 microns.

Figure 15:
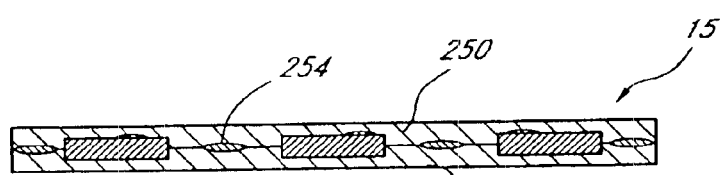
FIG. 15 is a cross sectional view through a composite barrier formed from the components illustrated in FIG. 14.

The composite stack is heated to a temperature of from about 200° to about 300°, for about 1 minute to about 5 minutes under pressure to provide a finished composite membrane assembly with an embedded frame 14 as illustrated schematically in FIG. 15. The final composite membrane has a thickness within the range of from about 0.001 inches to about 0.010 inches, and, preferably, is about 0.002 to about 0.003 inches in thickness. However, the thicknesses and process parameters of the foregoing may be varied considerably, depending upon the materials of the bonding layer 254 the first layer 250 and the second layer 252.

Figure 16:
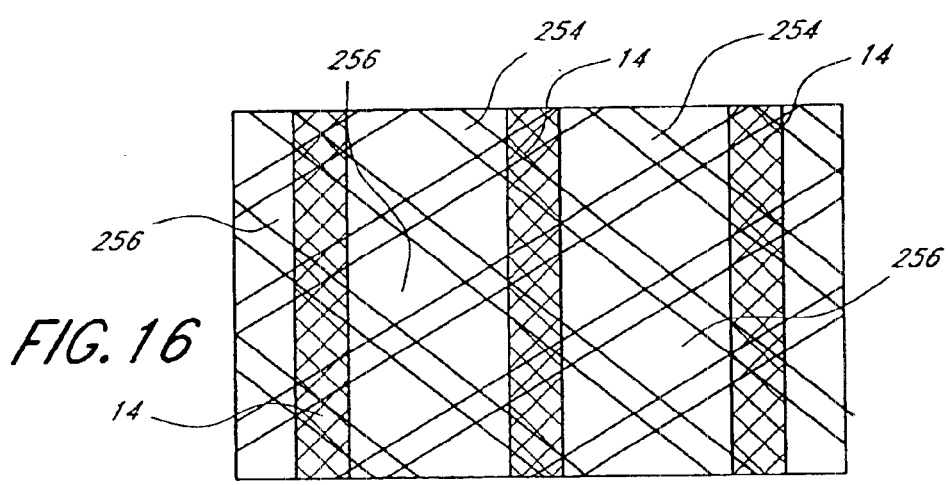
FIG. 16 is a top plan view of the composite barrier illustrated in FIG. 15.

As illustrated in top plan view in FIG. 16, the resulting finished composite membrane has a plurality of "unbonded" windows or areas 256 suitable for cellular attachment and/or ingrowth. The attachment areas 256 are bounded by the frame 14 struts, and the cross-hatch or other wall pattern formed by the bonding layer 254. Preferably, a regular window 256 pattern is produced in the bonding layer 254.

The foregoing procedure allows the bonding mesh to flow into the first and second membranes 250 and 252 and gives the composite membrane 15 greater strength (both tensile and tear strength) than the components without the bonding mesh. The composite allows uniform bonding while maintaining porosity of the membrane 15, to facilitate tissue attachment. By flowing the thermoplastic bonding layer into the pores of the outer mesh layers 250 and 252, the composite flexibility is preserved and the overall composite layer thickness can be minimized.

Referring back to FIGS. 1 and 2, the occlusion device 10 may be further provided with a bulking element or stabilizer 194. The stabilizer 194 may be spaced apart along an axis from the occluding member 11. In the illustrated embodiment, a distal end 190 and a proximal end 192 are identified for reference. The designation proximal or distal is not intended to indicate any particular anatomical orientation or deployment orientation within the deployment catheter. As shown in FIGS. 1 and 2, the stabilizer 194 is spaced distally apart from the occluding member 11.

For use in the LAA, the occluding member 11 has an expanded diameter within the range of from about 1 cm to about 5 cm, and, in one embodiment, about 3 cm. The axial length of the occluding member 11 in an expanded, unstressed orientation from the distal end 192 to the hub 16 is on the order of about 1 cm. The overall length of the occlusion device 10 from the distal end 192 to the proximal end 190 is within the range of from about 1.5 cm to about 4 cm and, in one embodiment, about 2.5 cm. The axial length of the stabilizer 194 between distal hub 191 and proximal hub 16 is within the range of from about 0.5 cm to about 2 cm, and, in one embodiment, about 1 cm. The expanded diameter of the stabilizer 194 is within the range of from about 0.5 cm to about 2.5 cm, and, in one embodiment, about 1.4 cm. The outside diameter of the distal hub 191 and proximal hub 16 is about 2.5 mm.

Preferably, the occlusion device 10 is provided with one or more retention structures for retaining the device in the left atrial appendage or other body cavity or lumen. In the illustrated embodiment, a plurality of barbs or other anchors 195 are provided, for engaging adjacent tissue to retain the occlusion device 10 in its implanted position and to limit relative movement between the tissue and the occlusion device. The illustrated anchors are provided on one or more of the spokes 17, or other portion of frame 14. Preferably, every spoke, every second spoke or every third spoke are provided with one or two or more anchors each.

The illustrated anchor is in the form of a barb, with one on each spoke for extending into tissue at or near the opening of the LAA. Depending upon the embodiment, two or three barbs may alternatively be desired on each spoke. In the single barb embodiment of FIG. 7, each barb is inclined in a proximal direction. This is to inhibit proximal migration of the implant out of the left atrial appendage. In this context, distal refers to the direction into the left atrial appendage, and proximal refers to the direction from the left atrial appendage into the heart.

Alternatively, one or more barbs may face distally, to inhibit distal migration of the occlusion device deeper into the LAA. Thus the implant may be provided with at least one proximally facing barb and at least one distally facing barb. For example, in an embodiment of the type illustrated in FIG. 12, discussed below, a proximal plurality of barbs may be inclined in a first direction, and a distal plurality of barbs may be inclined in a second direction, to anchor the implant against both proximal and distal migration.

One or more anchors 195 may also be provided on the stabilizer 194, such that it assists not only in orienting the occlusion device 10 and resisting compression of the LAA, but also in retaining the occlusion device 10 within the LAA. Any of a wide variety of structures may be utilized for anchor 195, either on the occluding member 11 or the stabilizer 194 or both, such as hooks, barbs, pins, sutures, adhesives, ingrowth surfaces and others which will be apparent to those of skill in the art in view of the disclosure herein.

In use, the occlusion device 10 is preferably positioned within a tubular anatomical structure to be occluded such as the left atrial appendage. In a left atrial appendage application, the occluding member 11 is positioned across or near the opening to the LAA and the stabilizer 194 is positioned within the LAA. The stabilizer 194 assists in the proper location and orientation of the occluding member 11, as well as resists compression of the LAA behind the occluding member 11. The present inventors have determined that following deployment of an occluding member 11 without a stabilizer 194 or other bulking structure to resist compression of the LAA, normal operation of the heart may cause compression and resulting volume changes in the LAA, thereby forcing fluid past the occluding member 11 and inhibiting or preventing a complete seal. Provision of a stabilizer 194 dimensioned to prevent the collapse or pumping of the LAA thus minimizes leakage, and provision of the barbs facilitates endothelialization or other cell growth across the occluding member 11.

The stabilizer 194 is preferably movable between a reduced cross-sectional profile for transluminal advancement into the left atrial appendage, and an enlarged cross-sectional orientation as illustrated to fill or to substantially fill a cross-section through the LAA. The stabilizing member may enlarge to a greater cross section than the (pre-stretched) anatomical cavity, to ensure a tight fit and minimize the likelihood of compression. One convenient construction includes a plurality of elements 196 which are radially outwardly expandable in response to axial compression of a distal hub 191 towards a proximal hub 16. Elements 196 each comprise a distal segment 198 and a proximal segment 202 connected by a bend 200. The elements 196 may be provided with a bias in the direction of the radially enlarged orientation as illustrated in FIG. 2, or may be radially expanded by applying an expansion force such as an axially compressive force between distal hub 191 and proximal hub 16 or a radial expansion force such as might be applied by an inflatable balloon. Elements 196 may conveniently be formed by laser cutting the same tube stock as utilized to construct the distal hub 191, proximal hub 16 and frame 14, as will be apparent to those of skill in the art in view of the disclosure herein. Alternatively, the various components of the occlusion device 10 may be separately fabricated or fabricated in subassemblies and secured together during manufacturing.

As a post implantation step for any of the occlusion devices disclosed herein, a radiopaque dye or other visualizable media may be introduced on one side or the other of the occlusion device, to permit visualization of any escaped blood or other fluid past the occlusion device. For example, in the context of a left atrial appendage application, the occlusion device may be provided with a central lumen or other capillary tube or aperture which permits introduction of a visualizable dye from the deployment catheter through the occlusion device and into the entrapped space on the distal side of the occlusion device. Alternatively, dye may be introduced into the entrapped space distal to the occlusion device such as by advancing a small gauge needle from the deployment catheter through the barrier 15 on the occlusion device, to introduce dye.

Figure 3:
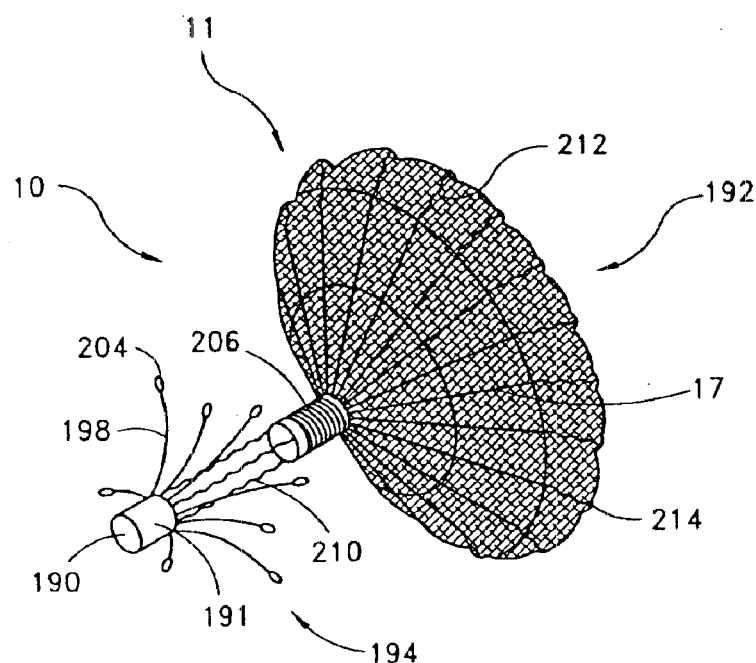
FIG. 3 is a perspective view of an alternate embodiment of the present invention.
Figure 4:
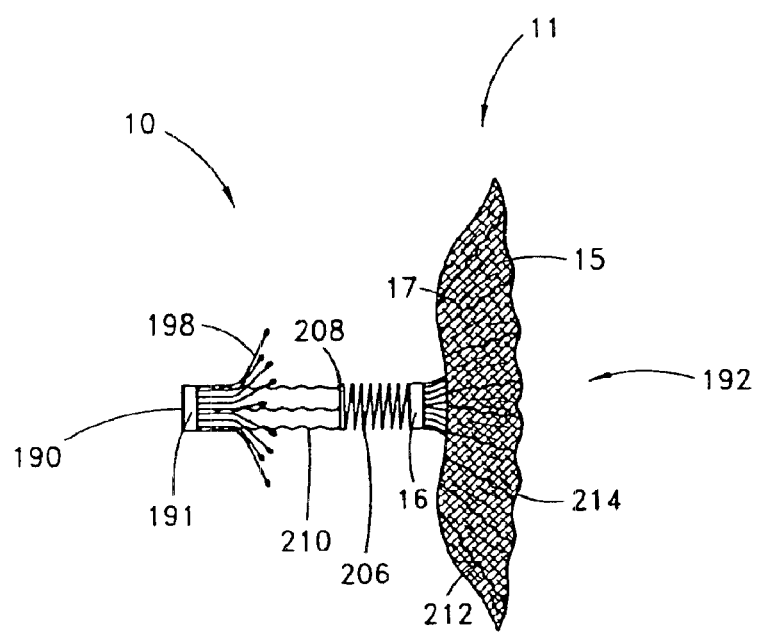
FIG. 4 is a side elevational view of the embodiment shown in FIG. 3.

Modifications to the occlusion device 10 are illustrated in FIGS. 3–4. The occlusion device 10 comprises an occlusion member 11 and a stabilizing member 194 as previously discussed. In the present embodiment, however, each of the distal segments 198 inclines radially outwardly in the proximal direction and terminates in a proximal end 204. The proximal end 204 may be provided with an atraumatic configuration, for pressing against, but not penetrating, the wall of the left atrial appendage or other tubular body structure. Three or more distal segments 198 are preferably provided, and generally anywhere within the range of from about 6 to about 20 distal segments 198 may be used. In one embodiment, 9 distal segments 198 are provided. In this embodiment, three of the distal segments 198 have an axial length of about 5 mm, and 6 of the distal segments 198 have an axial length of about 1 cm. Staggering the lengths of the distal segments 198 may axially elongate the zone in the left atrial appendage against which the proximal ends 204 provide anchoring support for the occlusion device.

The occlusion device 10 illustrated in FIGS. 3 and 4 is additionally provided with a hinge 206 to allow the longitudinal axis of the occlusion member 11 to be angularly oriented with respect to the longitudinal axis of the stabilizing member 194. In the illustrated embodiment, the hinge 206 is a helical coil, although any of a variety of hinge structures can be utilized. The illustrated embodiment may be conveniently formed by laser cutting a helical slot through a section of the tube from which the principal structural components of the occlusion device 10 are formed. At the distal end of the hinge 206, an annular band 208 connects the hinge 206 to a plurality of axially extending struts 210. In the illustrated embodiment, three axial struts 210 are provided, spaced equilaterally around the circumference of the body. Axial struts 210 may be formed from a portion of the wall of the original tube stock, which portion is left in its original axial orientation following formation of the distal segments 198 such as by laser cutting from the tubular wall.

The occlusion member 11 is provided with a proximal zone 212 on each of the spokes 17. Proximal zone 212 has an enhanced degree of flexibility, to accommodate the fit between the occlusion member 11 and the wall of the left atrial appendage. Proximal section 212 may be formed by reducing the cross sectional area of each of the spokes 17, which may be provided with a wave pattern as illustrated.

Each of the spokes 17 terminates in a proximal point 214. Proximal point 214 may be contained within layers of the barrier 15, or may extend through or beyond the barrier 15 such as to engage adjacent tissue and assist in retaining the occlusion device 10 at the deployment site.

Figure 5:
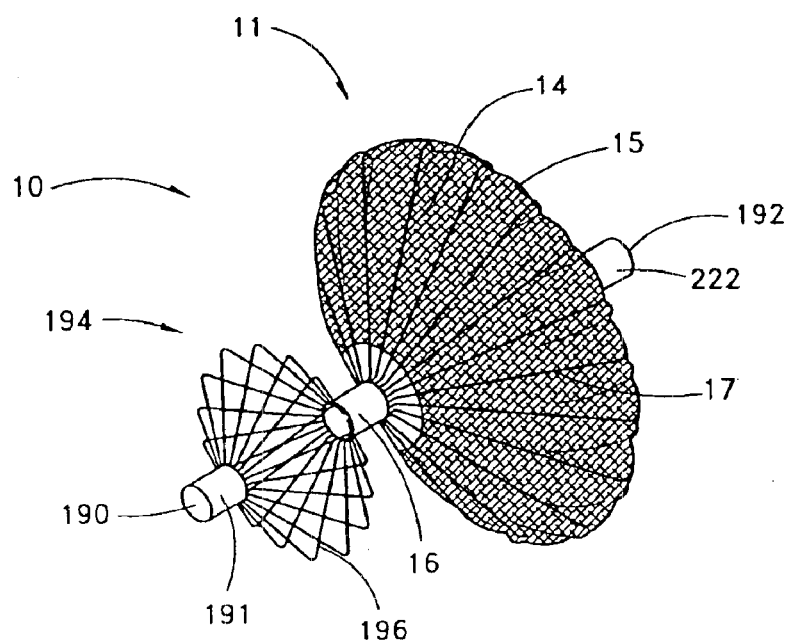
FIG. 5 is a perspective view of a further embodiment of the present invention.
Figure 6:
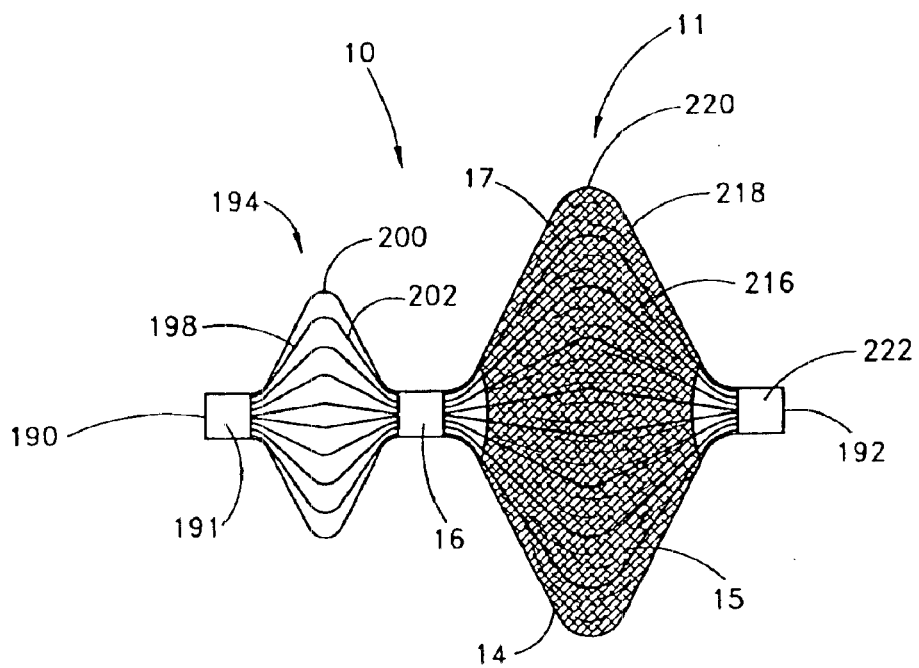
FIG. 6 is a side elevational view of the embodiment of FIG. 5.

Referring to FIGS. 5 and 6, a further variation on the occlusion device 10 illustrated in FIGS. 1 and 2 is provided.

The occlusion device 10 is provided with a proximal face 216 on the occlusion member 11, instead of the open and proximally concave face on the embodiment of FIGS. 1 and 2. The proximal face 216 is formed by providing a proximal spoke 218 which connects at an apex 220 to some or all of the distal spokes 17. The proximal spoke 218, and corresponding apex 220 and distal spoke 17 may be an integral structure, such as a single ribbon or wire, or element cut from a tube stock as has been discussed.

Proximal spokes 218 are each attached to a hub 222 at the proximal end 192 of the occlusion device 10. The barrier 15 may surround either the proximal face or the distal face or both on the occlusion member 11. In general, provision of a proximal spoke 218 connected by an apex 220 to a distal spoke 17 provides a greater radial force than a distal spoke 17 alone, which will provide an increased resistance to compression if the occlusion member 11 is positioned with the LAA.

Referring to FIGS. 7–12, alternate structures of the occlusion device in accordance with the present invention are illustrated. In general, the occlusion device 10 comprises an occluding member but does not include a distinct stabilizing member as has been illustrated in connection with previous embodiments. Any of the embodiments previously disclosed herein may also be constructed using the occluding member only, and omitting the stabilizing member as will be apparent to those of skill in the art in view of the disclosure herein.

The occluding device 10 comprises a proximal end 192, a distal end 190, and a longitudinal axis extending therebetween. A plurality of supports 228 extend between a proximal hub 222 and a distal hub 191. At least two or three supports 228 are provided, and preferably at least about ten. In one embodiment, sixteen supports 228 are provided. However, the precise number of supports 228 can be modified, depending upon the desired physical properties of the occlusion device 10 as will be apparent to those of skill in the art in view of the disclosure herein, without departing from the present invention.

Each support 228 comprises a proximal spoke portion 218, a distal spoke portion 17, and an apex 220 as has been discussed. Each of the proximal spoke portion 218, distal spoke portion 17 and apex 220 may be a region on an integral support 228, such as a continuous rib or frame member which extends in a generally curved configuration as illustrated with a concavity facing towards the longitudinal axis of the occlusion device 10. Thus, no distinct point or hinge at apex 220 is necessarily provided.

At least some of the supports 228, and, preferably, each support 228, is provided with one or two or more barbs 195. In the illustrated configuration; the occlusion device 10 is in its enlarged orientation, such as for occluding a left atrial appendage or other body cavity or lumen. In this orientation, each of the barbs 195 projects generally radially outwardly from the longitudinal axis, and is inclined in the proximal direction. One or more barbs may also be inclined distally, as is discussed elsewhere herein. In an embodiment where the barbs 195 and corresponding support 228 are cut from a single ribbon, sheet or tube stock, the barb 195 will incline radially outwardly at approximately a tangent to the curve formed by the support 228.

Figure 7B:
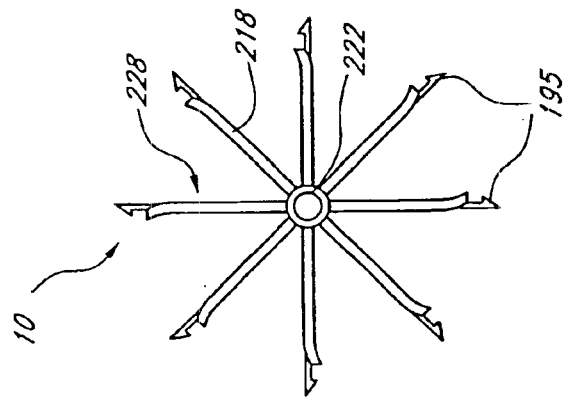
FIG. 7B is an end view taken along the line 7B—7B of FIG. 7A.
Figure 7A:
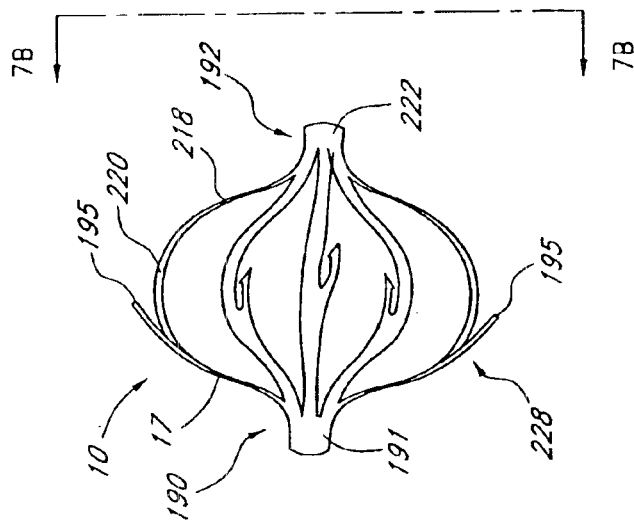
FIG. 7A is a side elevational view of the device of FIG. 7.
Figure 7:
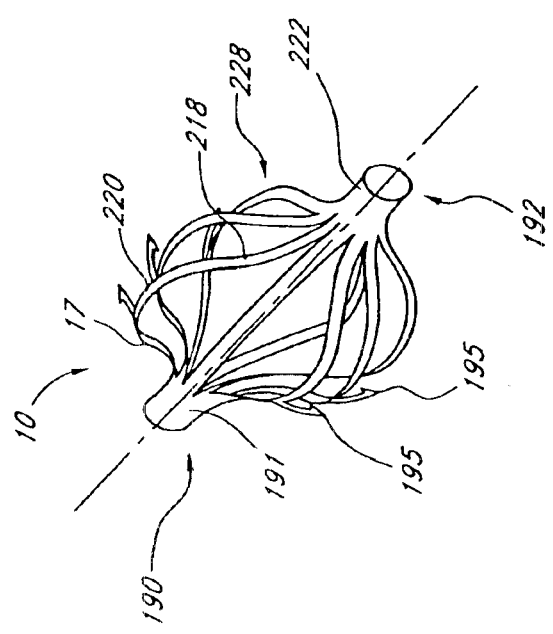
FIG. 7 is a perspective view of a support structure for a further occlusion device in accordance with the present invention.
Figure 9:
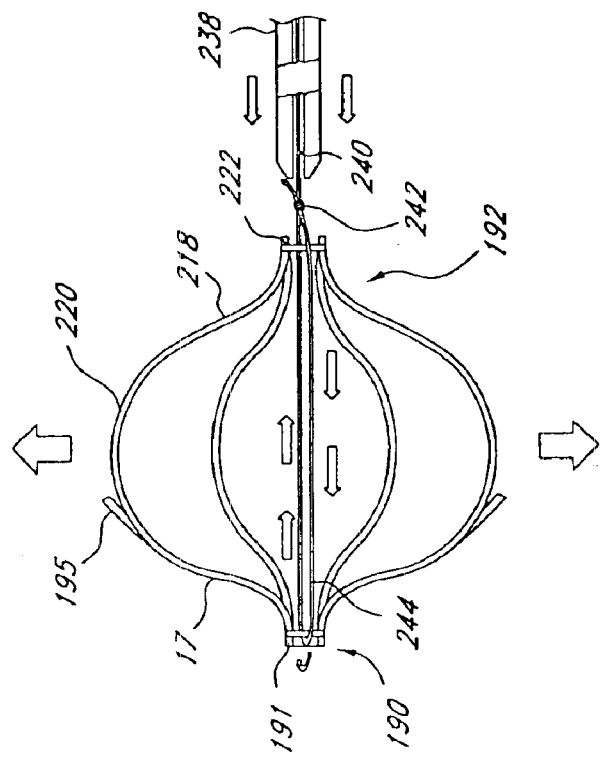
FIG. 9 is a schematic view of a pull string deployment embodiment of the occlusion device of FIG. 7.

The occlusion device 10 constructed from the frame illustrated in FIG. 7 may be constructed in any of a variety of ways, as will become apparent to those of skill in the art in view of the disclosure herein. In one method, the occlusion device 10 is constructed by laser cutting a piece of tube stock to provide a plurality of axially extending slots in-between adjacent supports 228. Similarly, each barb 195 can be laser cut from the corresponding support 228 or space in-between adjacent supports 228. The generally axially extending slots which separate adjacent supports 228 end a sufficient distance from each of the proximal end 192 and distal end 190 to leave a proximal hub 222 and a distal hub 191 to which each of the supports 228 will attach. In this manner, an integral cage structure may be formed. Alternatively, each of the components of the cage structure may be separately formed and attached together such as through soldering, brazing, heat bonding, adhesives, and other fastening techniques which are known in the art. A further method of manufacturing the occlusion device 10 is to laser cut a slot pattern on a flat sheet of appropriate material, such as a flexible metal or polymer, as has been discussed in connection with previous embodiments. The flat sheet may thereafter be rolled about an axis and opposing edges bonded together to form a tubular structure.

The apex portion 220 which carries the barb 195 may be advanced from a low profile orientation in which each of the supports 228 extend generally parallel to the longitudinal axis, to an implanted orientation as illustrated, in which the apex 220 and the barb 195 are positioned radially outwardly from the longitudinal axis. The support 228 may be biased towards the enlarged orientation, or may be advanced to the enlarged orientation under positive force following positioning within the tubular anatomical structure, in any of a variety of manners.

Figure 8:
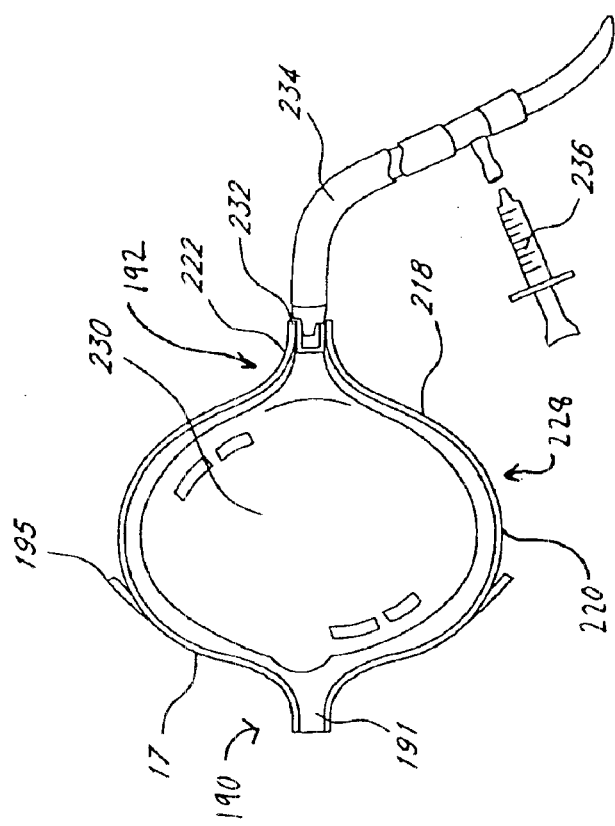
FIG. 8 is a schematic illustration of an inflatable balloon positioned within the occlusion device of FIG. 7.
Figure 13:
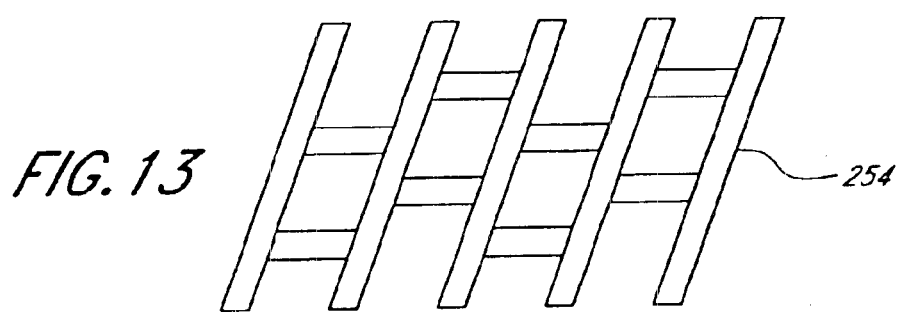
FIG. 13 is a schematic view of a bonding layer mesh for use in forming a composite barrier membrane in accordance with the present invention.

For an example of enlarging under positive force, referring to FIG. 8, an inflatable balloon 230 is positioned within the occlusion device 10. Inflatable balloon 230 is connected by way of a removable coupling 232 to an inflation catheter 234. Inflation catheter 234 is provided with an inflation lumen for providing communication between an inflation media source 236 outside of the patient and the balloon 230. Following positioning within the target body lumen, the balloon 230 is inflated, thereby engaging barbs 195 with the surrounding tissue. The inflation catheter 234 is thereafter removed, by decoupling the removable coupling 232, and the inflation catheter 234 is thereafter removed. The balloon 230 may be either left in place within the occlusion device 10, or deflated and removed by the inflation catheter 234.

In an alternate embodiment, the supports 228 are radially enlarged such as through the use of a deployment catheter 238. See FIG. 9. Deployment catheter 238 comprises a lumen for movably receiving a deployment element such as a flexible line 240. Deployment line 240 extends in a loop 244 formed by an aperture or slip knot 242. As will be apparent from FIG. 9, proximal retraction on the deployment line 240 while resisting proximal movement of proximal hub 222 such as by using the distal end of the catheter 238 will cause the distal hub 191 to be drawn towards the proximal hub 222, thereby radially enlarging the cross-sectional area of the occlusion device 10. Depending upon the material utilized for the occlusion device 10, the supports 228 will retain the radially enlarged orientation by elastic deformation, or may be retained in the enlarged orientation such as by securing the slip knot 242 immovably to the deployment line 240 at the fully radially enlarged orientation. This may be accomplished in any of a variety of ways, using additional knots, clips, adhesives, or other techniques known in the art.

A variety of alternative structures may be utilized, to open or enlarge the occlusion device 10 under positive force. For example, Referring to FIG. 9, a pullwire 240 may be removably attached to the distal hub 191 or other distal point of attachment on the occlusion device 10. Proximal retraction of the pullwire 240 while resisting proximal motion of the proximal hub 222 such as by using the distal end of the catheter 238 will cause enlargement of the occlusion device 10 as has been discussed. The pullwire 240 may then be locked with respect to the proximal hub 222 and severed or otherwise detached to enable removal of the deployment catheter 238 and proximal extension of the pullwire 240. Locking of the pullwire with respect to the proximal hub 222 may be accomplished in any of a variety of ways, such as by using interference fit or friction fit structures, adhesives, a knot or other technique depending upon the desired catheter design Referring to FIGS. 10 and 11, the occlusion device 10 may be provided with a barrier 15 such as a mesh or fabric as has been previously discussed. Barrier 15 may be provided on only one hemisphere such as proximal face 216, or may be carried by the entire occlusion device 10 from proximal end 192 to distal end 190. The barrier may be secured to the radially inwardly facing surface of the supports 228, as illustrated in FIG. 11, or may be provided on the radially outwardly facing surfaces of supports 228, or both.

A further embodiment of the occlusion device 10 is illustrated in FIG. 12, in which the apex 220 is elongated in an axial direction to provide additional contact area between the occlusion device 10 and the wall of the tubular structure. In this embodiment, one or two or three or more anchors 195 may be provided on each support 228, depending upon the desired clinical performance. The occlusion device 10 illustrated in FIG. 12 may also be provided with any of a variety of other features discussed herein, such as a partial or complete barrier 15. In addition, the occlusion device 10 illustrated in FIG. 12 may be enlarged using any of the techniques disclosed elsewhere herein.

Figure 17A:
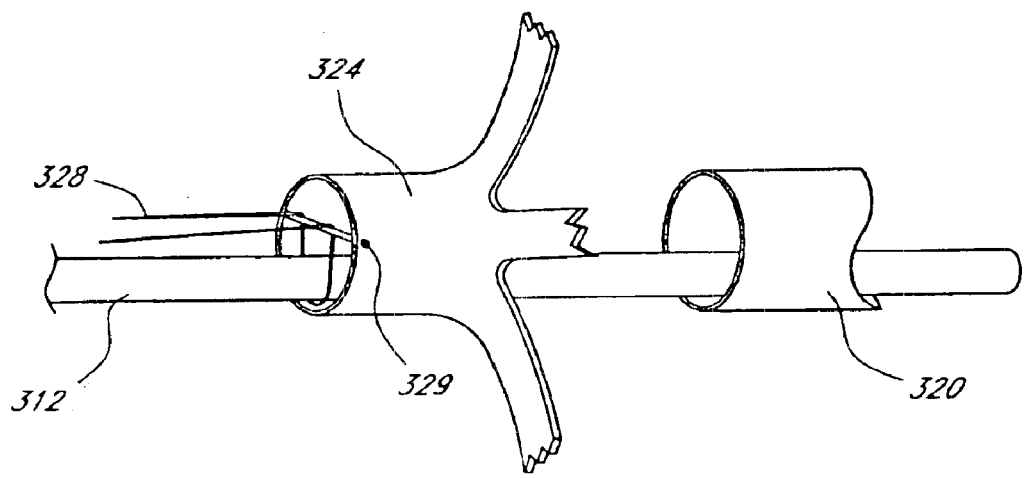
FIG. 17A is an enlarged view of a releasable lock in an engaged configuration
Figure 17B:
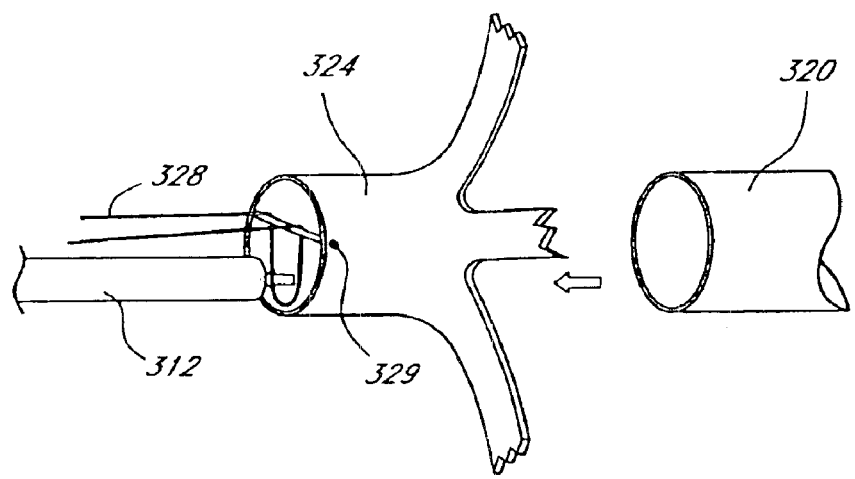
FIG. 17B is an enlarged view as in FIG. 17A, with the core axially retracted to release the implant.

Referring to FIG. 17, there is schematically illustrated a further aspect of the present invention. An adjustable implant deployment system 300 comprises generally a catheter 302 for placing a detachable implant 304 within a body cavity or lumen, as has been discussed. The catheter 302 comprises an elongate flexible tubular body 306, extending between a proximal end 308 and a distal end 310. The catheter is shown in highly schematic form, for the purpose of illustrating the functional aspects thereof. The catheter body will have a sufficient length and diameter to permit percutaneous entry into the vascular system, and transluminal advancement through the vascular system to the desired deployment site. For example, in an embodiment intended for access at the femoral artery and deployment within the left atrial appendage, the catheter 302 will have a length within the range of from about 50 cm to about 150 cm, and a diameter of generally no more than about 15 French. Further dimensions and physical characteristics of catheters for navigation to particular sites within the body are well understood in the art and will not be further described herein.

The tubular body 306 is further provided with a handle 309 generally on the proximal end 308 of the catheter 302. The handle 309 permits manipulation of the various aspects of the implant deployment system 300, as will be discussed below. Handle 309 may be manufactured in any of a variety of ways, typically by injection molding or otherwise forming a handpiece for single-hand operation, using materials and construction techniques well known in the medical device arts.

The implant 304 may be in the form of any of those described previously herein, as modified below. In general, the implant is movable from a reduced crossing profile to an enlarged crossing profile, such that it may be positioned within a body structure and advanced from its reduced to its enlarged crossing profile to obstruct bloodflow or perform other functions while anchored therein. The implant 304 may be biased in the direction of the enlarged crossing profile, may be neutrally biased or may be biased in the direction of the reduced crossing profile. Any modifications to the device and deployment system to accommodate these various aspects of the implant 304 may be readily accomplished by those of skill in the art in view of the disclosure herein.

In the illustrated embodiment, the distal end 314 of the implant 304 is provided with an implant plug 316. Implant plug 316 provides a stopping surface 317 for contacting an axially movable core 312. The core 312 extends axially throughout the length of the catheter body 302, and is attached at its proximal end to a core control 332 on the handle 309.

The core 312 may comprise any of a variety of structures which has sufficient lateral flexibility to permit navigation of the vascular system, and sufficient axial column strength to enable reduction of the implant 304 to its reduced crossing profile. Any of a variety of structures such as hypotube, solid core wire, "bottomed out" coil spring structures, or combinations thereof may be used, depending upon the desired performance of the finished device. In one embodiment, the core 312 comprises stainless steel tubing.

The distal end of core 312 is positioned within a recess or lumen 322 defined by a proximally extending guide tube 320. In the illustrated embodiment, the guide tube 320 is a section of tubing such as metal hypotube, which is attached at the distal end 314 of the implant and extends proximally within the implant 304. The guide tube 320 preferably extends a sufficient distance in the proximal direction to inhibit buckling or prolapse of the core 312 when distal pressure is applied to the core control 332 to reduce the profile of the implant 304. However, the guide tube 320 should not extend proximally a sufficient distance to interfere with the opening of the implant 304.

As will be appreciated by reference to FIG. 17, the guide tube 320 may operate as a limit on distal axial advancement of the proximal end 324 of implant 304. Thus, the guide tube 320 preferably does not extend sufficiently far proximally from the distal end 314 to interfere with optimal opening of the implant 304. The specific dimensions are therefore relative, and will be optimized to suit a particular intended application. In one embodiment, the implant 304 has an implanted outside diameter within the range of from about 5 mm to about 45 mm, and an axial implanted length within the range of from about 5 mm to about 45 mm. The guide tube 320 has an overall length of about 3 mm to about 35 mm, and an outside diameter of about 0.095 inches.

An alternate guide tube 320 is schematically illustrated in FIG. 18. In this configuration, the guide tube 320 comprises a plurality of tubular segments 321 spaced apart by an intervening space 323. This allows increased flexibility of the guide tube 320, which may be desirable during the implantation step, while retaining the ability of the guide tube 320 to maintain linearity of the core 312 while under axial pressure. Although three segments 321 are illustrated in FIG. 18, as many as 10 or 20 or more segments 321 may be desirable depending upon the desired flexibility of the resulting implant.

Each adjacent pair of segments 321 may be joined by a hinge element 325 which permits lateral flexibility. In the illustrated embodiment, the hinge element 325 comprises an axially extending strip or spine, which provides column strength along a first side of the guide tube 320. The guide tube 320 may therefore be curved by compressing a second side of the guide tube 320 which is generally offset from the spine 325 by about 180°. A limit on the amount of curvature may be set by adjusting the axial length of the space 323 between adjacent segments 321. In an embodiment having axial spines 325, each axial spine 325 may be rotationally offset from the next adjacent axial spine 325 to enable flexibility of the overall guide tube 320 throughout a 360° angular range of motion.

Alternatively, the flexible hinge point between each adjacent segment 321 may be provided by cutting a spiral groove or plurality of parallel grooves in a tubular element in between what will then become each adjacent pair of segments 321. In this manner, each tubular element 321 will be separated by an integral spring like structure, which can permit flexibility. As a further alternative, the entire length of the guide tube 320 may comprise a spring. Each of the forgoing embodiments may be readily constructed by laser cutting or other cutting from a piece of tube stock, to produce a one piece guide tube 320. Alternatively, the guide tube 320 may be assembled from separate components and fabricated together using any of a variety of bonding techniques which are appropriate for the construction material selected for the tube 320.

Various distal end 314 constructions may be utilized, as will be apparent to those of skill in the art in view of the disclosure herein. In the illustrated embodiment, the distal implant plug 316 extends within the implant 304 and is attached to the distal end of the guide tube 320. The implant plug 316 may be secured to the guide tube 320 and implant 304 in any of a variety of ways, depending upon the various construction materials. For example, any of a variety of metal bonding techniques such as a welding, brazing, interference fit such as threaded fit or snap fit, may be utilized. Alternatively, any of a variety of bonding techniques for dissimilar materials may be utilized, such as adhesives, and various molding techniques. In one construction, the implant plug 316 comprises a molded polyethylene cap, and is held in place utilizing a distal cross pin 318 which extends through the implant 304, the guide tube 320 and the implant plug 316 to provide a secure fit against axial displacement.

The proximal end 324 of the implant 304 is provided with a releasable lock 326 for attachment to a release element such as pull wire 328. Pull wire 328 extends proximally throughout the length of the tubular body 306 to a proximal pull wire control 330 on the handle 309.

As used herein, the term pull wire is intended to include any of a wide variety of structures which are capable of transmitting axial tension or compression such as a pushing or pulling force with or without rotation from the proximal end 308 to the distal end 310 of the catheter 302. Thus, monofilament or multifilament metal or polymeric rods or wires, woven or braided structures may be utilized. Alternatively, tubular elements such as a concentric tube positioned within the outer tubular body 306 may also be used as will be apparent to those of skill in the art.

In the illustrated embodiment, the pull wire 328 is releasably connected to the proximal end 324 of the implant 304. This permits proximal advancement of the proximal end of the implant 304, which cooperates with a distal retention force provided by the core 312 against the distal end of the implant to axially elongate the implant 304 thereby reducing it from its implanted configuration to its reduced profile for implantation. The proximal end of the pull wire 328 may be connected to any of a variety of pull wire controls 330, including rotational knobs, levers and slider switches, depending upon the design preference.

The proximal end 324 of the implant 304 is thus preferably provided with a releasable lock 326 for attachment of the pullwire 328 to the deployment catheter. In the illustrated embodiment, the releasable lock is formed by advancing the pullwire distally around a cross pin 329, and providing an eye or loop which extends around the core 312. As long as the core 312 is in position within the implant 304, proximal retraction of the pullwire 328 will advance the proximal end 324 of the implant 304 in a proximal direction. See FIG. 17A. However, following deployment, proximal retraction of the core 312 such as by manipulation of the core control 332 will pull the distal end of the core 312 through the loop on the distal end of the pullwire 328. The pullwire 328 may then be freely proximally removed from the implant 304, thereby enabling detachment of the implant 304 from the deployment system 300 within a treatment site. See FIG. 17B.

The implant deployment system 300 thus permits the implant 304 to be maintained in a low crossing profile configuration, to enable transluminal navigation to a deployment site. Following positioning at or about the desired deployment site, proximal retraction of the core 312 enables the implant 304 to radially enlarge under its own bias to fit the surrounding tissue structure. Alternatively, the implant can be enlarged under positive force, such as by inflation of a balloon or by a mechanical mechanism as is discussed elsewhere herein. Once the clinician is satisfied with the position of the implant 304, such as by injection of dye and visualization using conventional techniques, the core 312 is proximally retracted thereby releasing the lock 326 and enabling detachment of the implant 304 from the deployment system 300.

If, however, visualization reveals that the implant 304 is not at the location desired by the clinician, proximal retraction of the pull wire 328 with respect to the core 312 will radially reduce the diameter of the implant 304, thereby enabling repositioning of the implant 304 at the desired site. Thus, the present invention permits the implant 304 to be enlarged or reduced by the clinician to permit repositioning and/or removal of the implant 304 as may be desired.

Figure 19:
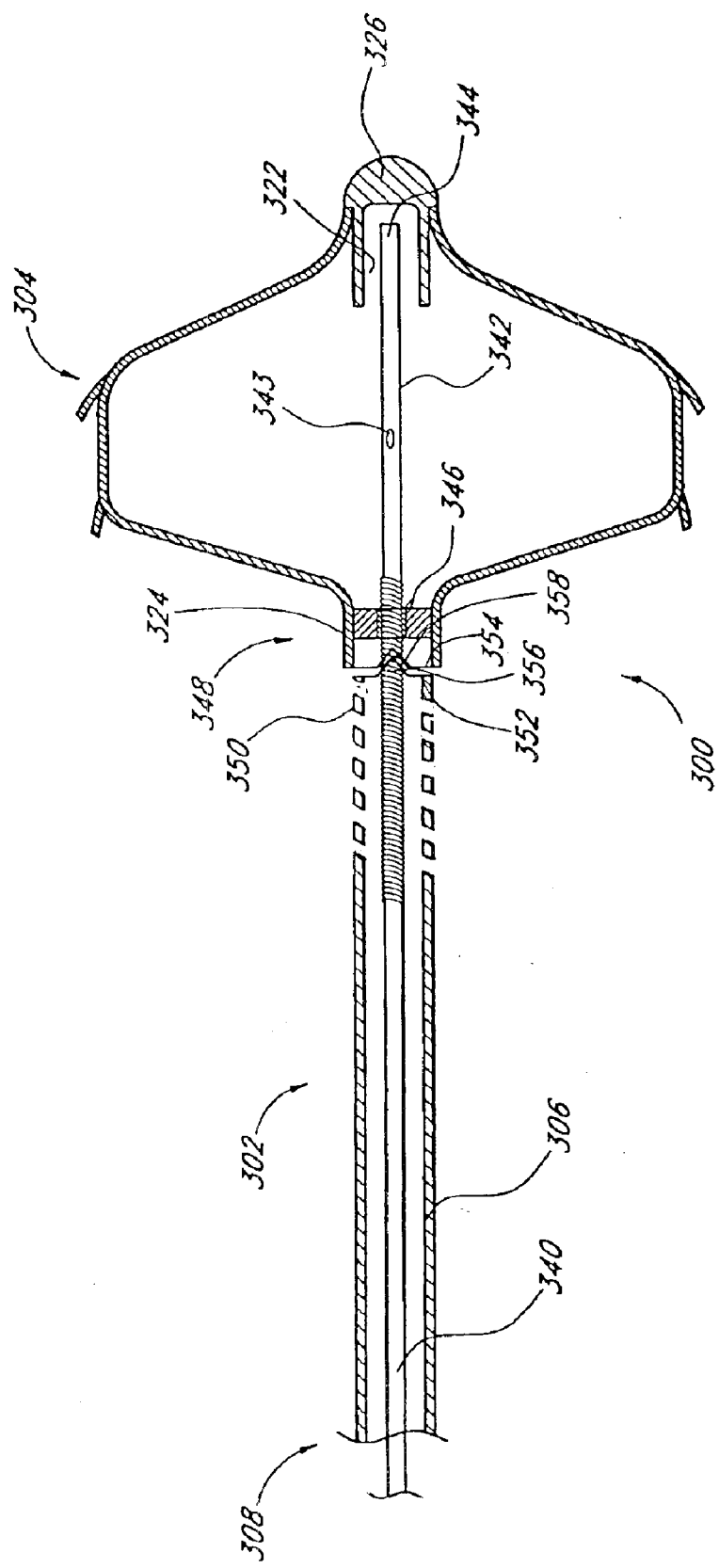
FIG. 19 is a schematic view of an alternate deployment system in accordance with the present invention.

In an alternate construction, the implant may be radially enlarged or reduced by rotating a torque element extending throughout the deployment catheter. Referring to FIG. 19, the elongate flexible tubular body 306 of the deployment catheter 302 includes a rotatable torque rod 340 extending axially therethrough. The proximal end of the torque rod 340 may be connected at a proximal manifold to a manual rotation device such as a hand crank, thumb wheel, rotatable knob or the like. Alternatively, the torque rod 340 may be connected to a power driven source of rotational energy such as a motor drive or air turbine.

The distal end of the torque rod 340 is integral with or is connected to a rotatable core 342 which extends axially through the implant 304. A distal end 344 of the rotatable core 342 is positioned within a cavity 322 as has been discussed.

The terms torque rod or torque element are intended to include any of a wide variety of structures which are capable of transmitting a rotational torque throughout the length of a catheter body. For example, solid core elements such as stainless steel, nitinol or other nickel titanium alloys, or polymeric materials may be utilized. In an embodiment intended for implantation over a guide-wire, the torque rod 340 is preferably provided with an axially extending central guidewire lumen. This may be accomplished by constructing the torque rod 340 from a section of hypodermic needle tubing, having an inside diameter of from about 0.001 inches to about 0.005 inches or more greater than the outside diameter of the intended guidewire. Tubular torque rods 340 may also be fabricated or constructed utilizing any of a wide variety of polymeric constructions which include woven or braided reinforcing layers in the wall. Torque transmitting tubes and their methods of construction are well understood in the intracranial access and rotational atherectomy catheter arts, among others, and are not described in greater detail herein. Use of a tubular torque rod 340 also provides a convenient infusion lumen for injection of contrast media within the implant 304, such as through a port 343.

The proximal end 324 of the implant 304 is provided with a threaded aperture 346 through which the core 342 is threadably engaged. As will be appreciated by those of skill in the art in view of the disclosure herein, rotation of the threaded core 342 in a first direction relative to the proximal end 324 of the implant 304 will cause the rotatable core 342 to advance distally. This distal advancement will result in an axial elongation and radial reduction of the implantable device 304. Rotation of the rotatable core 342 in a reverse direction will cause a proximal retraction of the rotatable core 342, thus enabling a radial enlargement and axial shortening of the implantable device 304.

The deployment catheter 302 is further provided with an antirotation lock 348 between a distal end 350 of the tubular body 306 and the proximal end 324 of the implant 304. In general, the rotational lock 348 may be conveniently provided by cooperation between a first surface 352 on the distal end 350 of the deployment catheter 302, which engages a second surface 354 on the proximal end 324 of the implantable device 304, to rotationally link the deployment catheter 302 and the implantable device 304. Any of a variety of complementary surface structures may be provided, such as an axial extension on one of the first and second surfaces for coupling with a corresponding recess on the other of the first and second surfaces. Such extensions and recesses may be positioned laterally offset from the axis of the catheter. Alternatively, they may be provided on the longitudinal axis with any of a variety of axially releasable anti-rotational couplings having at least one flat such as a central hexagonal or other multifaceted cross sectional configuration.

Figure 19A:
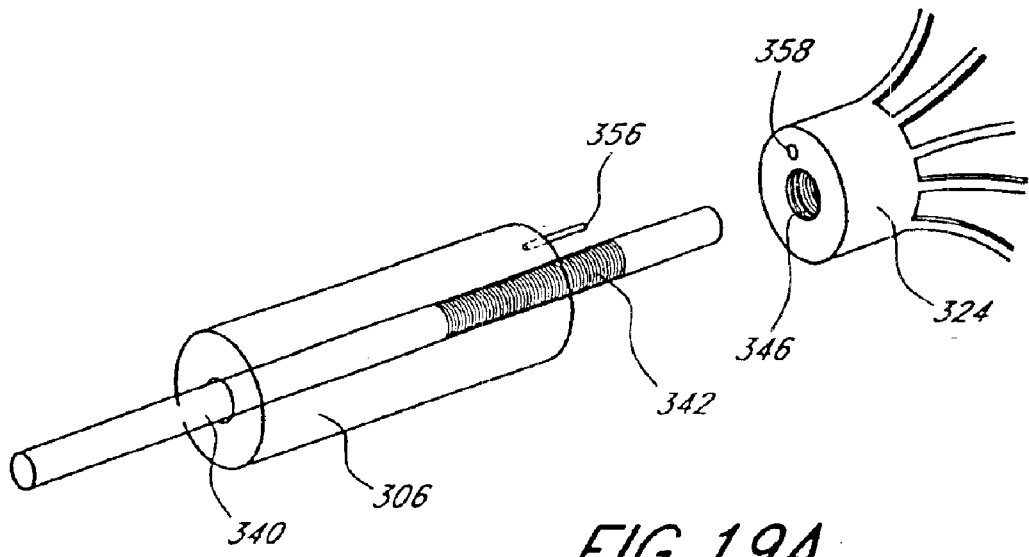
FIGS. 19A–B illustrate a removal sequence for an implanted device in accordance with the present invention.
Figure 19B:
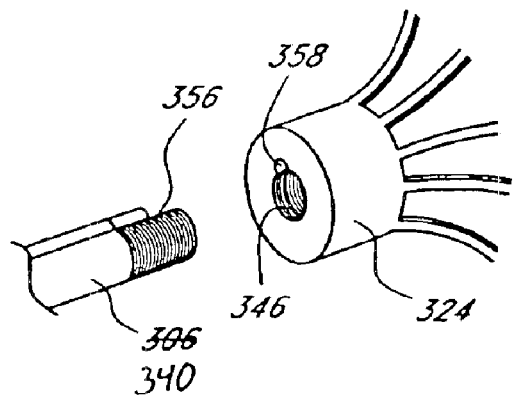

As schematically illustrated in FIG. 19, one or more projections 356 on the first surface 352 may engage a corresponding recess 358 on the second surface 354. Any of a variety of alternative complementary surface structures may also be provided, as will be apparent to those of skill in the art in view of the disclosure herein. For example, referring to FIG. 19A, the projection 356 is in the form of an axially extending pin for engaging a complimentary recess 358 on the proximal end 324 of the implant 304. FIG. 19B illustrates an axially extending spline 356 for receipt within a complimentary axially extending recess 358. The various pin, spline and other structures may be reversed between the distal end of tubular body 306 and the proximal end 324 of the implant 304 as will be apparent to those of skill in the art in view of the disclosure herein.

Upon placement of the implantable device 304 at the desired implantation site, the torque rod 340 is rotated in a direction that produces an axial proximal retraction. This allows radial enlargement of the radially outwardly biased implantable device 304 at the implantation site. Continued rotation of the torque rod 340 will cause the threaded core 342 to exit proximally through the threaded aperture 346. At that point, the deployment catheter 302 may be proximally retracted from the patient, leaving the implanted device 304 in place.

By modification of the decoupling mechanism to allow the core 342 to be decoupled from the torque rod 340, the rotatable core 342 may be left within the implantable device 304, as may be desired depending upon the intended deployment mechanism. For example, the distal end of the core 342 may be rotatably locked within the end cap 326, such as by including complimentary radially outwardly or inwardly extending flanges and grooves on the distal end of the core 342 and inside surface of the cavity 322. In this manner, proximal retraction of the core 342 by rotation thereof relative to the implantable device 304 will pull the end cap 326 in a proximal direction under positive force. This may be desirable as a supplement to or instead of a radially enlarging bias built into the implantable device 304.

In the embodiment illustrated in FIG. 19, or any other of the deployment and/or removal catheters described herein, the distal end of the tubular body 306 may be provided with a zone or point of enhanced lateral flexibility. This may be desirable in order allow the implant to seat in the optimal orientation within the left atrial appendage, and not be restrained by a lack of flexibility in the tubular body 306. This may be accomplished in any of a variety of way, such as providing the distal most one or two or three centimeters or more of the tubular body 306 with a spring coil configuration. In this manner, the distal end of the tubular body 306 will be sufficiently flexible to allow the implant 304 to properly seat within the LAA. This distal flex zone on the tubular body 306 may be provided in any of a variety of ways, such as by cutting a spiral slot in the distal end of the tubular body 306 using laser cutting or other cutting techniques. The components within the tubular body 306 such as torque rod 340 may similarly be provided with a zone of enhanced flexibility in the distal region of the tubular body 306.

Figure 20:
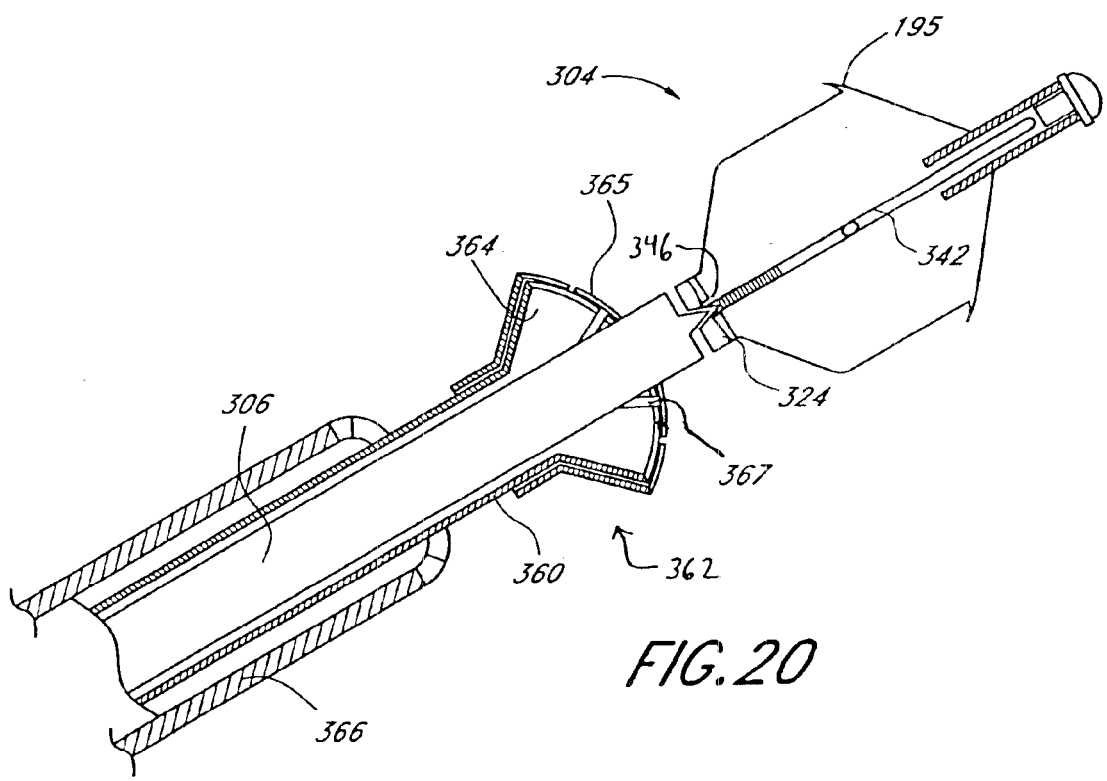
FIG. 20 is a schematic cross sectional view through the distal end of a retrieval catheter having an occlusion device removably connected thereto.

The implantable device 304 may also be retrieved and removed from the body in accordance with a further aspect of the present invention. One manner of retrieval and removal will be understood in connection with FIGS. 20 through 20c. Referring to FIG. 20, a previously implanted device 304 is illustrated as releasably coupled to the distal end of the tubular body 306, as has been previously discussed. Coupling may be accomplished by aligning the tubular body 306 with the proximal end 324 of the deployed implant 304, under fluoroscopic visualization, and distally advancing a rotatable core 342 through the threaded aperture 346. Threadable engagement between the rotatable core 342 and aperture 346 may thereafter be achieved, and distal advancement of core 342 will axially elongate and radially reduce the implant 304.

The tubular body 306 is axially moveably positioned within an outer tubular delivery or retrieval catheter 360. Catheter 360 extends from a proximal end (not illustrated) to a distal end 362. The distal end 362 is preferably provided with a flared opening, such as by constructing a plurality of petals 364 for facilitating proximal retraction of the implant 304 as will become apparent. Petals 364 may be constructed in a variety of ways, such as by providing axially extending slits in the distal end 362 of the delivery catheter 360. In this manner, preferably at least about three, and generally at least about four or five or six petals or more will be provided on the distal end 362 of the delivery catheter 360. Petals 364 manufactured in this manner would reside in a first plane, transverse to the longitudinal axis of the delivery catheter 360, if each of such petals 364 were inclined at 90 degrees to the longitudinal axis of the delivery catheter 360.

In one application of the invention, a second layer of petals 365 are provided, which would lie in a second, adjacent plane if the petals 365 were inclined at 90 degrees to the longitudinal axis of the delivery catheter 360. Preferably, the second plane of petals 365 is rotationally offset from the first plane of petals 364, such that the second petals 365 cover the spaces 367 formed between each adjacent pair of petals 365. The use of two or more layers of staggered petals 364 and 365 has been found to be useful in retrieving implants 304, particularly when the implant 304 carries a plurality of tissue anchors 195.

The petals 364 and 365 may be manufactured from any of a variety of polymer materials useful in constructing medical device components such as the delivery catheter 360. This includes, for example, polyethylene, PET, PEEK, PEBAX, and others well known in the art. The second petals 365 may be constructed in any of a variety of ways. In one convenient construction, a section of tubing which concentrically fits over the delivery catheter 360 is provided with a plurality of axially extending slots in the same manner as discussed above. The tubing with a slotted distal end may be concentrically positioned on the catheter 360, and rotated such that the space between adjacent petals 365 is offset from the space between adjacent petals 364. The hub of the petals 365 may thereafter be bonded to the catheter 360, such as by heat shrinking, adhesives, or other bonding techniques known in the art.

Figure 20A:
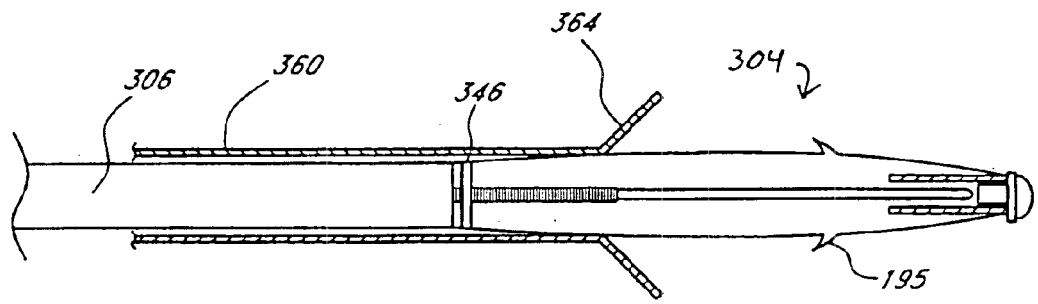
FIG. 20A is a side elevational schematic view of the system illustrated in FIG. 20, with the occlusion device axially elongated and radially reduced.
Figure 20B:
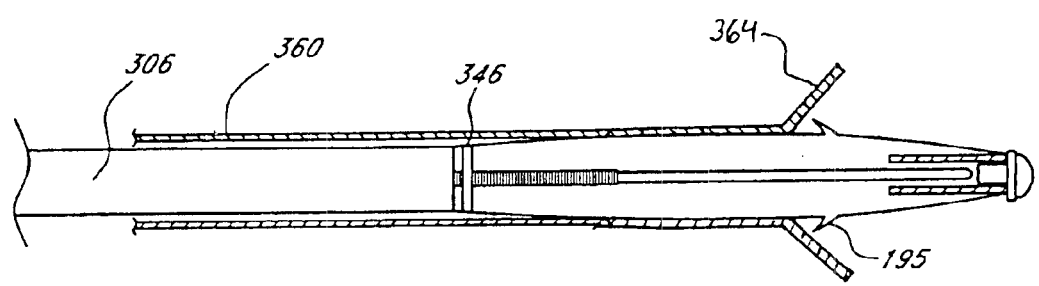
FIG. 20B is a side elevational schematic view as in FIG. 20A, with the occlusion device drawn part way into the delivery catheter.
Figure 20C:
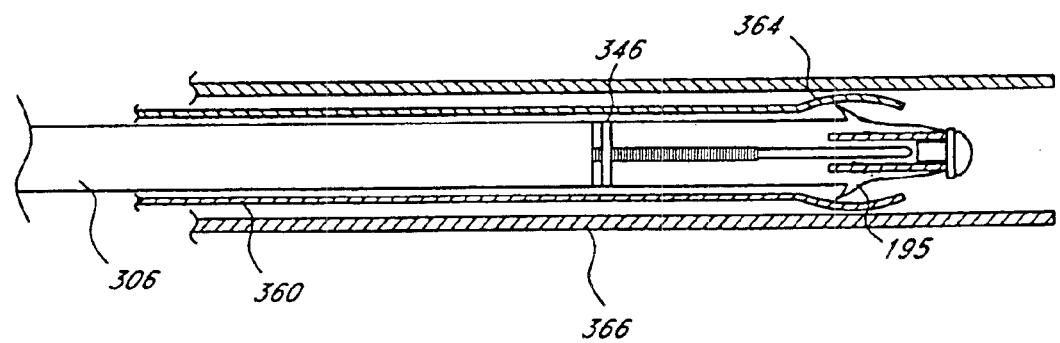
FIG. 20C is a schematic view as in FIG. 20B, with the occlusion device and delivery catheter drawn into a transseptal sheath.

The removal sequence will be further understood by reference to FIGS. 20a through 20c. Referring to FIG. 20a, the radially reduced implant 304 is proximally retracted part way into the delivery catheter 360. This can be accomplished by proximally retracting the tubular body 306 and/or distally advancing the catheter 360. As illustrated in FIG. 20b, the tubular body 306 having the implant 304 attached thereto is proximally retracted a sufficient distance to position the tissue anchors 195 within the petals 364. The entire assembly of the tubular body 306, within the delivery catheter 360 may then be proximally retracted within the transeptal sheath 366 or other tubular body as illustrated in FIG. 20c. The collapsed petals 364 allow this to occur while preventing engagement of the tissue anchors 195 with the distal end of the transeptal sheath 366 or body tissue. The entire assembly having the implantable device 304 contained therein may thereafter be proximally withdrawn from or repositioned within the patient.

While particular forms of the invention have been described, it will be apparent that various modifications can be made without departing from the spirit and scope of the invention. Accordingly, it is not intended that the invention be limited, except as by the appended claims.

What is claimed is:

1. A method of implanting a device in the left atrial appendage, comprising the steps of:
    providing a deployment catheter, having an elongate flexible body with a proximal end and a distal end, a control on the proximal end and a device removably carried adjacent the distal end;
    positioning at least a portion of the device in the left atrial appendage; and
    manipulating the control to enlarge the device under positive force;
    wherein the device comprises an expandable frame comprising at least two spokes, wherein the spokes are cut from a tube.

2. A method as in claim 1, wherein the manipulating step comprises rotating the control.

3. A method as in claim 1, wherein the frame comprises at least six spokes.

4. A method as in claim 3, wherein each spoke is movable from an axial orientation when the device is in a reduced cross section to an inclined orientation when the device is in an enlarged cross section.

5. A method as in claim 4, wherein each spoke comprises a proximal section, a distal section, and a bend in between the proximal and distal sections when the device is in the enlarged cross section.

6. A method as in claim 1, wherein the device further comprises a plurality of tissue anchors, and the method comprises the step of engaging tissue with at least some of the tissue anchors.

7. A method of implanting a device in the left atrial appendage, comprising:
    providing a catheter having an elongate flexible body with a proximal end and a distal end, and an implantable device removably carried adjacent the distal end;
    positioning at least a portion of the device in the left atrial appendage; and
    enlarging the device within the left atrial appendage,
    wherein the catheter comprises a deployment element extending therethrough releasably connected to the device.

8. The method of claim 7, wherein the deployment element comprises a flexible line.

9. The method of claim 7, wherein the deployment element comprises a core.

10. The method of claim 7, wherein the deployment element comprises a pull wire.

11. The method of claim 7, wherein the deployment element is controlled by proximal retraction of the deployment element.

12. The method of claim 7, wherein the elongate flexible body comprises a lumen through which the deployment elements is provided.

13. The method of claim 7, wherein enlarging the device within the left atrial appendage axially shortens the device.

14. The method of claim 7, wherein the device comprises a proximal hub and a distal hub.

15. The method of claim 14, wherein enlarging the device within the left atrial appendage comprises proximally retracting the distal hub while resisting movement of the proximal hub.

16. The method of claim 7, wherein the device self-expands to its enlarged shape.

17. The method of claim 7, further comprising releasing the device after the device is enlarged within the left atrial appendage.

18. A method for implanting a device in the left atrial appendage of a patient, comprising:
    providing an implantable device having a proximal end and a distal end, the implantable device having a collapsed configuration and an expanded configuration;
    positioning the implantable device in the left atrial appendage while the device is in its collapsed configuration; and
    expanding the implantable device in the left atrial appendage, wherein the device is enlarged by providing relative movement between a proximal end and a distal end of the device.

19. The method of claim 18, wherein expanding the implantable device comprises drawing the proximal and distal ends of the device relatively closer together.

20. The method of claim 18, wherein expansion of the device is at least partially controlled by a deployment line connected to one of the ends of the implantable device and extending through a deployment catheter.

21. The method of claim 20, wherein the deployment line is releasably connected to a proximal end of the implantable device.

22. The method of claim 20, wherein the deployment line is releasably connected to a distal end of the implantable device.

23. The method of claim 18, further comprising an inner member extending through a deployment catheter and extending to the distal end of the implantable device.

24. The method of claim 18, wherein the implantable device is at least partially self-expanding.

25. A method for implanting a device in the left atrial appendage of a patient, comprising:
providing an implantable device having a proximal end and a distal end, the implantable device having a collapsed configuration and an expanded configuration;
positioning the implantable device in the left atrial appendage while the device is in its collapsed configuration; and
expanding the implantable device in the left atrial appendage, wherein the device is enlarged by providing relative movement between a proximal end and a distal end of the device;
wherein a core extends through a deployment catheter and extends to the distal end of the implantable device, and wherein relative movement between the proximal and distal ends of the implantable device is provided by moving the core in a proximal direction.

26. A method for implanting a device in the left atrial appendage of a patient, comprising:
providing an implantable device having a proximal end and a distal end, the implantable device having a collapsed configuration and an expanded configuration;
positioning the implantable device in the left atrial appendage while the device is in its collapsed configuration; and
expanding the implantable device in the left atrial appendage, wherein the device is enlarged by providing relative movement between a proximal end and a distal end of the device;
wherein a core extends through a deployment catheter and extends to the distal end of the implantable device, and wherein the implantable device is maintained in its collapsed configuration while being positioned in the left atrial appendage by holding stationary one end of the device while moving the other end of the device.

27. A method for implanting a device in the left atrial appendage of a patient, comprising:
providing an implantable device having a proximal end and a distal end, the implantable device having a collapsed configuration and an expanded configuration;
positioning the implantable device in the left atrial appendage while the device is in its collapsed configuration, the implantable device when delivered into the left atrial appendage being releasably connected to a deployment line extending outside of the patient; and
expanding the implantable device in the left atrial appendage;
wherein the deployment line is releasably connected to and looped around a portion of the implantable device.

28. The method of claim 27, wherein the implantable device is delivered to the left atrial appendage using a catheter.

29. A method for implanting a device in the left atrial appendage of a patient, comprising:
providing an implantable device having a proximal end and a distal end, the implantable device having a collapsed configuration and an expanded configuration;
positioning the implantable device in the left atrial appendage while the device is in its collapsed configuration, the implantable device when delivered into the left atrial appendage being releasably connected to a deployment line extending outside of the patient;
expanding the implantable device in the left atrial appendage; and
releasing the deployment line from the implantable device after the implantable device is appropriately expanded in the left atrial appendage;
wherein the deployment line is releasably connected to a proximal end of the implantable device, wherein the deployment line is a pull wire boned around a pin at the proximal end of the implantable device, and wherein the pull wire is looped over the pin and around a core extending through the implantable device.

30. A method for delivering an implantable device within a left atrial appendage of a patient, comprising:
providing a deployment catheter having a proximal end and a distal end, the deployment catheter having an elongate core and a pull wire extending therethrough;
delivering an implantable device having a proximal end and a distal end to the left atrial appendage using the deployment catheter, the implantable device having a collapsed configuration wherein the proximal and distal ends are relatively far apart and an expanded configuration wherein the proximal and distal ends are relatively close together, the proximal end releasably connected to the pull wire and the distal end engaged with the elongate core, wherein the pull wire is held taut and the elongate core is pushed against a distal surface of the implantable device to hold the implantable device in its collapsed configuration during delivery; and
expanding the implantable device within the left atrial appendage by moving the elongate core proximally relative to the proximal end of the device and the pull wire, the proximal movement causing the implantable device to expand under its own bias to the expandable configuration.

31. The method of claim 30, further comprising at least partially collapsing the implantable device after expanding the implantable device to reposition the implantable device by moving the elongate core relatively distally against the distal surface and moving the pull wire relatively proximally causing the proximal and distal ends of the implantable device to move relatively apart.

32. The method of claim 30, wherein the elongate core slides relative to the implantable device within a guide tube extending axially within the implantable device.

33. The method of claim 30, further comprising removing the elongate core and the pull wire from the implantable device after confirming the position of the implantable device within the left atrial appendage.

34. The method of claim 30, wherein the pull wire is releasably locked to the implantable device by looping the pull wire around a pin at the proximal end of the device and around the core.

35. The method of claim 30, wherein the core is threadingly engageable with a portion of the implantable device.

36. The method of claim 30, wherein the elongate core provides a distal retention force against the distal end of the implantable device, and wherein expanding the implantable device within the left atrial appendage by moving the elongate core proximally relative to the proximal end of the device and the pull wire comprises manipulating the pull wire while maintaining the distal retention force such that the implantable device expands under its own bias, drawing the proximal end of the device toward the distal end.

37. A method for implanting a device in the left atrial appendage of a patient, comprising:

providing an implantable device having a proximal end and a distal end, the implantable device having a collapsed configuration and an expanded configuration;

positioning the implantable device in the left atrial appendage while the device is in its collapsed configuration, the implantable device when delivered into the left atrial appendage being releasably connected to a deployment line extending outside of the patient; and expanding the implantable device in the left atrial appendage.

38. The method of claim 37, wherein the deployment line is releasably connected to a proximal end of the implantable device.

39. The method of claim 37, wherein the implantable device is delivered to the left atrial appendage using a catheter.

* * * * *

UNITED STATES PATENT AND TRADEMARK OFFICE
CERTIFICATE OF CORRECTION

PATENT NO. : 7,044,134 B2  
APPLICATION NO. : 10/033371  
DATED : May 16, 2006  
INVENTOR(S) : Alexander K. Khairkhahan et al.

Page 1 of 1

It is certified that error appears in the above-identified patent and that said Letters Patent is hereby corrected as shown below:

Title Page;

(60) Related U.S. Application Data delete  "Division of application No. 10/033,371, filed on Oct. 19, 2001, which is"

Signed and Sealed this
Thirtieth Day of August, 2011

David J. Kappos
*Director of the United States Patent and Trademark Office*